US011110185B2

(12) United States Patent
Meijer et al.

(10) Patent No.: US 11,110,185 B2
(45) Date of Patent: Sep. 7, 2021

(54) COMBINATION FORMULATION

(71) Applicant: GE Healthcare AS, Nydalen (NO)

(72) Inventors: Andreas Richard Meijer, Oslo (NO); Mikkel Jacob Thaning, Oslo (NO); Paritosh Jayant Dhawale, Brookfield, WI (US); Salvatore Desena, Marlborough, MA (US); Paul Alexander Jones, Buckinghamshire (GB); Deirdre Cassidy, Buckinghamshire (GB); Concetta Valeria Gringeri, Buckinghamshire (GB)

(73) Assignee: GE HEALTHCARE AS, Oslo (NO)

( * ) Notice: Subject to any disclaimer, the term of this patent is extended or adjusted under 35 U.S.C. 154(b) by 0 days.

(21) Appl. No.: 15/768,831

(22) PCT Filed: Nov. 30, 2016

(86) PCT No.: PCT/EP2016/079311
§ 371 (c)(1),
(2) Date: Apr. 16, 2018

(87) PCT Pub. No.: WO2017/093336
PCT Pub. Date: Jun. 8, 2017

(65) Prior Publication Data
US 2018/0303960 A1    Oct. 25, 2018

Related U.S. Application Data

(60) Provisional application No. 62/260,804, filed on Nov. 30, 2015.

(51) Int. Cl.
*A61K 49/10* (2006.01)

(52) U.S. Cl.
CPC .......... *A61K 49/105* (2013.01); *A61K 49/101* (2013.01); *A61K 49/108* (2013.01); *A61K 2123/00* (2013.01)

(58) Field of Classification Search
CPC .. A61K 49/101; A61K 49/103; A61K 49/105; A61K 49/106; A61K 49/108; A61K 2123/00
See application file for complete search history.

(56) References Cited

U.S. PATENT DOCUMENTS

| | | | | |
|---|---|---|---|---|
| 5,215,680 A * | 6/1993 | D'Arrigo | ............. | A61K 9/5015 424/405 |
| 8,192,721 B2 | 6/2012 | Rowe | | |
| 2009/0297008 A1 | 12/2009 | Taxt et al. | | |
| 2015/0283272 A1* | 10/2015 | Kundra | ............. | A61K 49/1812 424/1.21 |
| 2016/0045623 A1* | 2/2016 | Kaufman | ............. | A61B 5/055 424/9.32 |

FOREIGN PATENT DOCUMENTS

| | | | |
|---|---|---|---|
| JP | 2007536048 A | 12/2007 | |
| JP | 2009537201 A | 10/2009 | |
| WO | 2005106517 A2 | 11/2005 | |
| WO | 2007132242 A1 | 11/2007 | |
| WO | 2009103744 A2 | 8/2009 | |
| WO | 2017093336 A1 | 6/2017 | |

OTHER PUBLICATIONS

Bannas et al., Magnetic Resonance in Medicine, 2016, 75, p. 318-328. (Year: 2016).*
Clinicaltrials.gov archive, https://clinicaltrials.gov/ct2/history/NCT02156739?A=1&B=1&C=Side-by-Side#StudyPageTop, Jun. 3, 2014. (Year: 2014).*
EOVIST (Gadoxetate Disodium) Injection for intravenous use (Dec. 2010). (Year: 2010).*
Schelhorn et al., Acta Radiologica, 2016, 57(8), p. 932-938. (Year: 2015).*
International Search Report and the Written Opinion of the International Searching Authority, or the Declaration from International Appl. No. PCT/EP2016/079311, dated Feb. 16, 2017.
Benoit Dupas et al., "Delineation of Liver Necrosis Using Double Contrast-Enhanced MRI," Journal of Magnetic Resonance Imaging, Society for Magnetic Resonance Imaging, vol. 7, No. 13, Jan. 1997, pp. 472-477.
Krishna Kattel et al., "Paramagnetic Dysprosium Oxide Nanoparticles and Dysprosium Hydroxide Nanorods as T2 MRI Contrast Agents," Biomaterials, Elsevier Science Publishers BV., vol. 33, No. 11, Jan. 2012, pp. 3254-3261.
Ahmed Ba-Ssalama et al., "Clinical Value of MRI Liver-Specific Contrast Agents: A Tailored Examination for a Confident Non-Invasive Diagnosis of Focal Liver Lesions," European Radiology, vol. 19, No. 2, Sep. 2008, pp. 342-357.
R. Golfieri et al., "Ruolo della RM a Doppio Contrasto Rispetto alla TC Multidetettore Nella Diagnosi del Piccola Epatocarcinoma (≤3 cm) su Cirrosi," Radiologia Medica, vol. 114, No. 8, Aug. 2009, pp. 1239-1266.

(Continued)

*Primary Examiner* — Michael G. Hartley
*Assistant Examiner* — Leah H Schlientz
(74) *Attorney, Agent, or Firm* — Jeff B. Vockrodt; Culhane Meadows, PLLC

(57) ABSTRACT

The present invention relates to in vivo imaging and in particular to magnetic resonance imaging (MRI). Provided by the present invention is a pharmaceutical formulation suitable for use in an MRI procedure and which offers advantages over known such formulations. A particular dose of the pharmaceutical formulation of the invention is also envisioned as well as the use of said dose in a method of in vivo imaging. This present invention provides for simultaneous administration of a liver specific agent and a second MR contrast agent that is capable of better/further enhancing the dynamic vascular phase in a patient. The method of the invention has the advantage of simplicity and patient comfort, compared to sequential injections. Furthermore, the method of the invention provides the advantage that it can enable a lower cumulative dose of contrast agents.

28 Claims, 9 Drawing Sheets

(56) References Cited

OTHER PUBLICATIONS

Chinese First Office Action received in Application No. 201680069678.2 dated Sep. 28, 2020, 15 pages.
Chinese Search Report received in Application No. 201680069678.2 dated Sep. 21, 2020, 6 pages.
"History of Changes for Study: NCT02156739, Liver Lesions in Contract-Enhanced Magnetic Resonance Imaging (MRI)," dated Dec. 19, 2019, 4 pages.
Bannas, et al., "Combined Gadoxetic Acid and Gadofosveset Enhanced Liver MRI: A Feasibility and Parameter Optimization Study," Preclinical and Clinical Imaging, Magnetic Resonance in Medicine 75: 318-328, 2016 [no date], 11 pages.
Japanese Office Action received in Application No. 2018-527102 dated Dec. 11, 2020, 10 pages.
Shah, et al., "Evaluation of meglumine gadoterate-enhanced MR angiography (MRA) compared with time-of-flight MRA in the diagnosis of clinically significant non-coronary arterial disease: a pooled analysis of data from two clinical trials," Aug. 31, 2010, 10 pages.
Office Action received in Chinese Application No. 201680069678.2 dated Jun. 22, 2021, with translation, 14 pages.
Search Report received in Chinese Application No. 201680069678.2 dated Jun. 9, 2021, with translation, 6 pages.

* cited by examiner

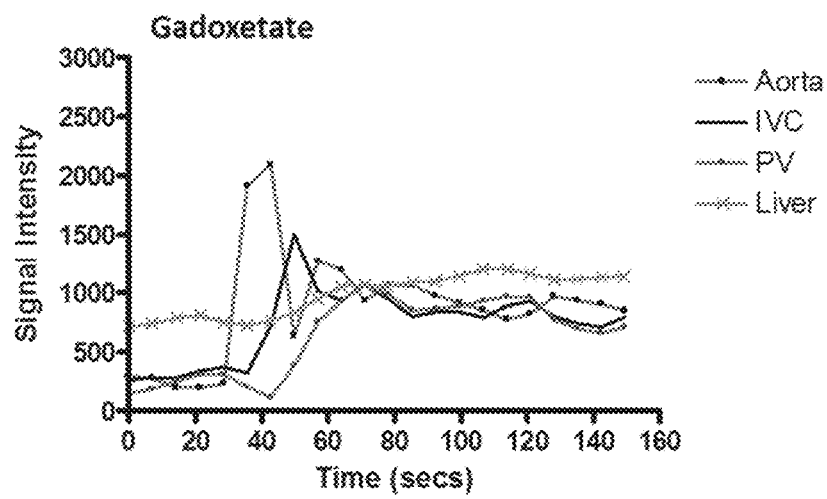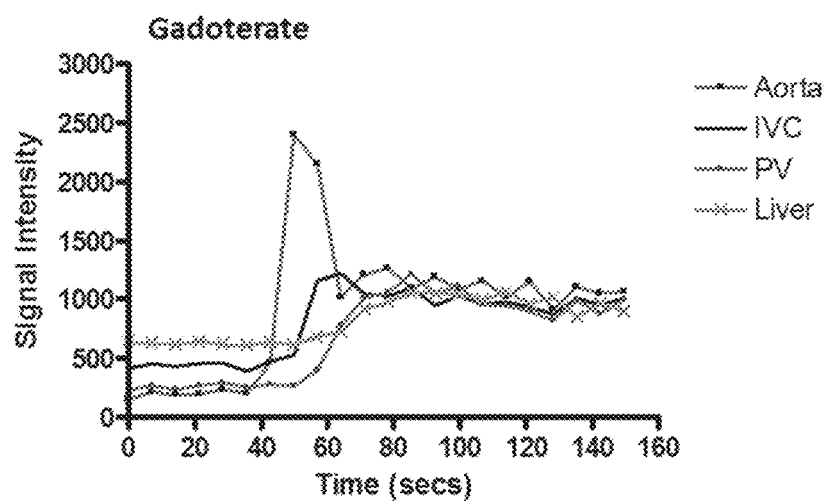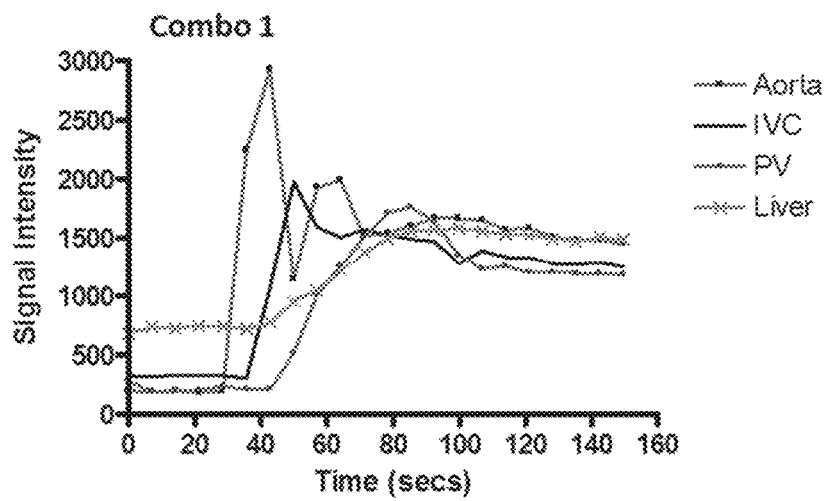
Figures 3A-C

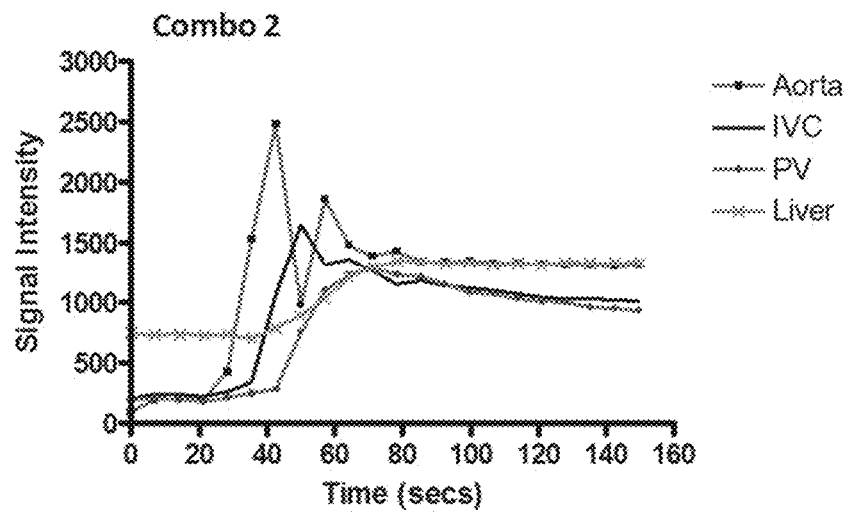
D
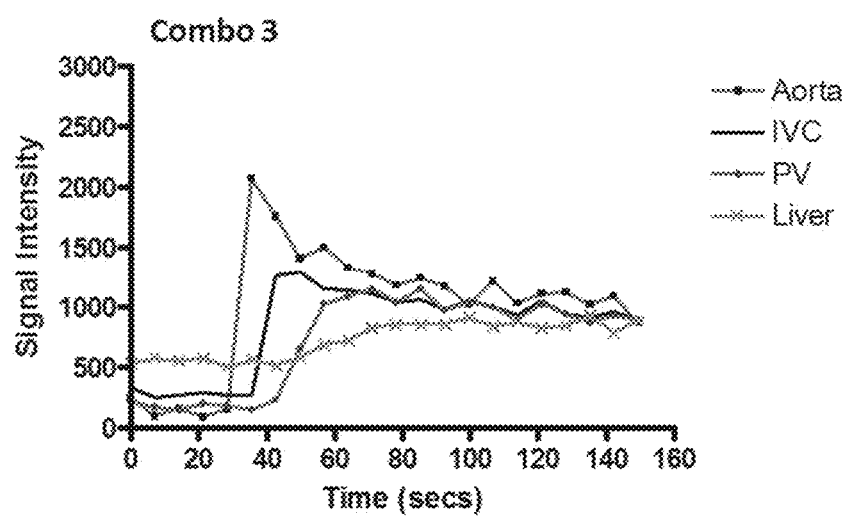
E
Figures 3D-E

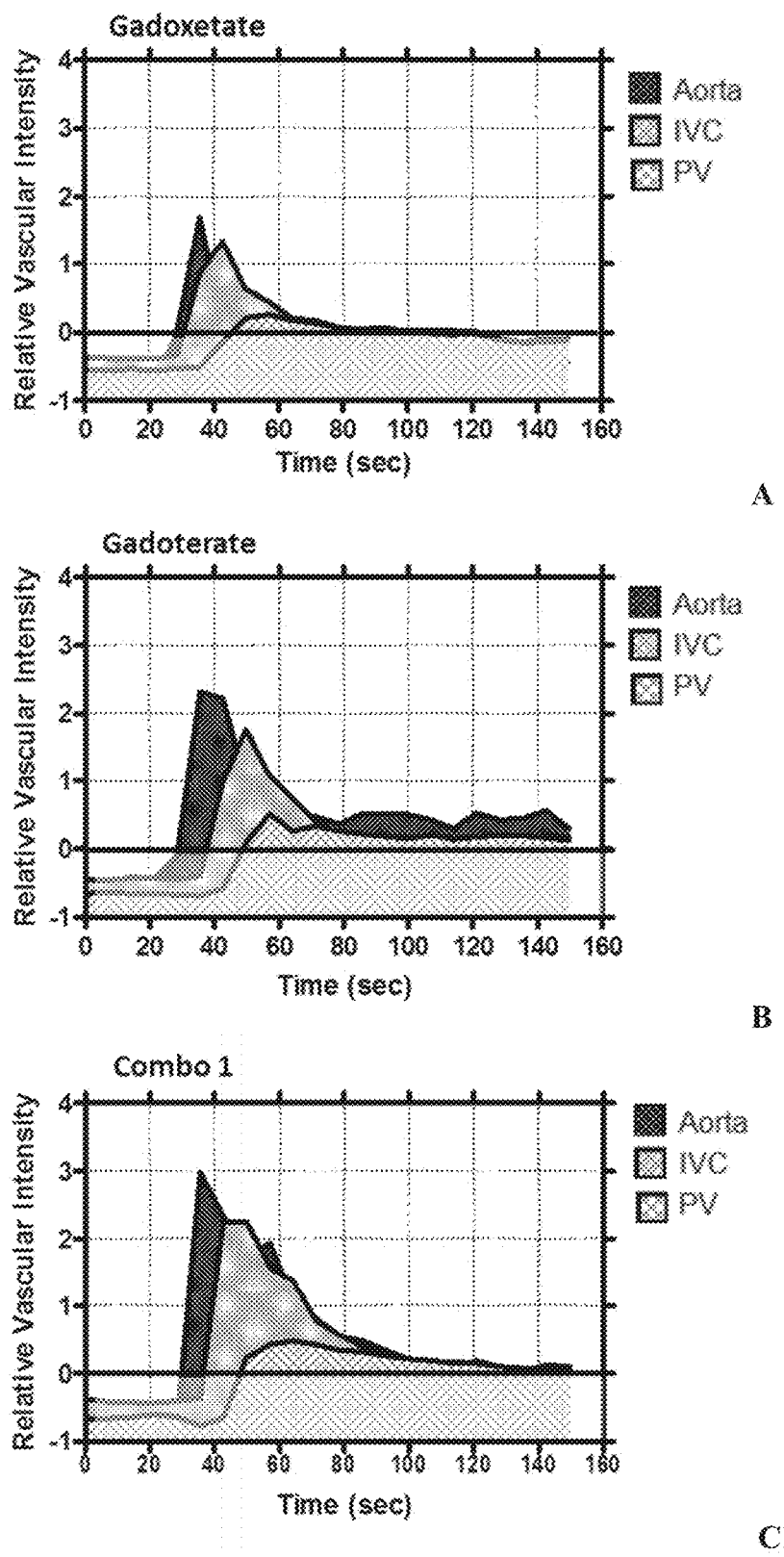
Figure 4A-C

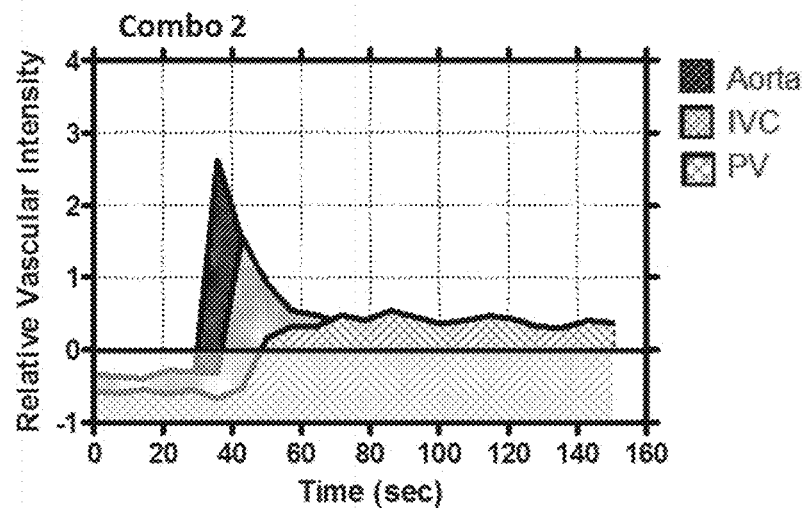
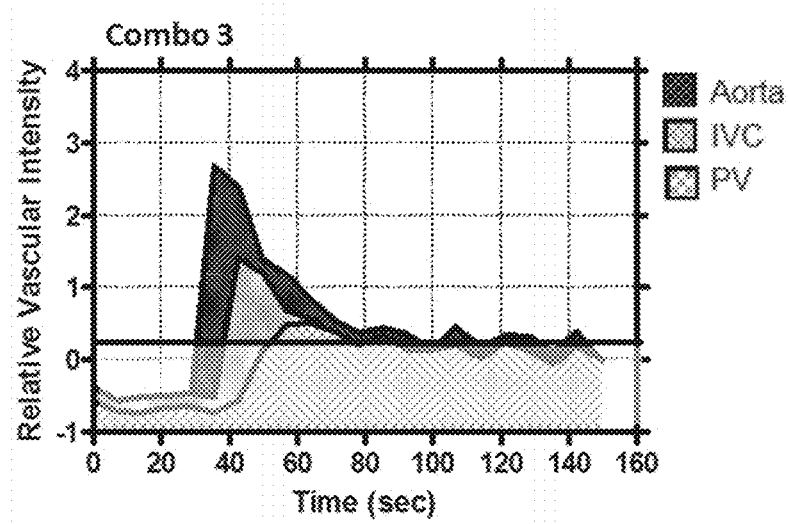
Figure 4D-E

COMBINATION FORMULATION

TECHNICAL FIELD OF THE INVENTION

The present invention relates to in vivo imaging and in particular to magnetic resonance imaging (MRI). Provided by the present invention is a pharmaceutical formulation suitable for use in an MRI procedure and which offers advantages over other known such formulations. A particular dose of the pharmaceutical formulation of the invention is also envisioned as well as the use of said dose in a method of in vivo imaging.

DESCRIPTION OF RELATED ART

Gadoxetate (Gd-EOB-DTPA, Primovist in Europe and Eovist in the USA) is a liver-specific magnetic resonance imaging contrast agent that has up to 50% hepatobiliary excretion in the normal liver. After intravenous injection, gadoxetate distributes into the vascular and extravascular spaces and progressively into the hepatocytes and bile ducts during the arterial, portal venous and hepatobiliary phases. Gadoxetate behaves similarly to non-specific gadolinium chelates during the arterial and portal venous phases, and adds substantial information during the hepatobiliary phase, improving the detection and characterization of focal liver lesions and diffuse liver disease (Beers et al 2012 J Hepatol; 57 (2): 421-429).

However, it is well recognized that gadoxetate suffers from an overall poor dynamic vascular phase (comprises arterial phase "AP", portal venous phase "PVP" and late venous phase "LVP") compared to non-specific gadolinium chelates (Frydrychowicz et al 2012 JMRI; 35 (3): 492-511). Possible remedies to this include using higher doses of gadoxetate, slowing the rate of gadoxetate injection, or an additional injection of a general purpose (nonspecific) agent known to better enhance the dynamic vascular phase.

Zech et al. (2009 Investigat Radiol; 44 (6): 305-310) evaluated a slow injection rate (or "bolus stretch") and demonstrated a favourable bolus shape with a standard clinical dose of gadoxetate. This bolus stretch compensates for the lower gadolinium amount in the single dose of gadoxetate with a potential improvement in the AP at the early part of the dynamic vascular phase. However the compensation effect is not extended to the venous vessels (i.e. PVP and LVP) and the extracellular enhancement of the liver parenchyma. Instead, the lower amount of gadolinium is related to a significantly lower signal increase in these structures compared with either a double dose of gadoxetate or a single dose of a general purpose extracellular Gd based contrast agent (Gd-DTPA). Zech et al. demonstrated that enhancement in the PVP and LVP was not influenced significantly by the injection rate, but did improve with a double dose of gadoxetate. This latter approach would mean a double dose of gadolinium, which is not without drawbacks.

In an approach proposed by Bayer (clinical trial NCT02156739) patients received 0.1 mmol/kg of the general purpose agent gadopentetate dimeglumine 20 minutes post-administration of 0.025 mmol/kg gadoxetate. The additional injection of an extracellular agent 20 min post the administration of gadoxetate generates signal intensity of the liver vasculature to a level comparable to the gadoxetate enhanced liver, thereby rendering the liver plain white (with bright healthy hepatocytes and bright vessels). This approach aims to generate a uniform enhanced organ to improve lesion characterisation but does nothing to improve the relatively poor dynamic vascular phase of gadoxetate.

There is a need for improved methods to overcome the issues relating to poor dynamic phase imaging of gadoxetate.

SUMMARY OF THE INVENTION

In a first aspect the present invention provides a pharmaceutical preparation comprising:
(i) a first active pharmaceutical ingredient (API) having hepatocellular uptake and biliary excretion; and,
(ii) a second API having renal excretion;
wherein each of said first API and said second API is a metal chelate comprising a chelant and a paramagnetic metal ion, and wherein the ratio of said first API to said second API is from 1:10 to 4:1.

The present invention also provides in a second aspect a dose of a pharmaceutical preparation to be administered to a subject wherein said pharmaceutical preparation is as defined herein and wherein said dose comprises between 0.01-0.04 mmol per kilogram of said subject of said first API and between 0.01-0.1 mmol per kilogram of said subject of said second API with the proviso that the combined dose of said first API and second API does not exceed 0.125 mmol per kilogram of said subject.

In a third aspect the present invention provides a method comprising:
(a) administering a dose of a pharmaceutical composition to a subject wherein said dose is as defined herein;
(b) carrying out magnetic resonance imaging (MRI) on said subject following said administering step wherein magnetic resonance (MR) signals are detected from the subject or parts of the subject into which the composition has distributed;
(c) generating MR images and/or MR spectra from the detected MR signals.

It is known that the dynamic vascular phase after bolus injection of an MRI contrast agent is of high importance for accurate visualization of normal vascular structures and the assessment of their relation to pathologic processes for diagnosis and treatment planning. The present invention demonstrates an improvement in sustained vascular enhancement across all vascular phases especially in the late PVP and LVP with a comparative delayed post-vascular phase to the liver specific agent. The additional vascular signal is useful in liver lesion characterisation and could facilitate vascular biomarker profiling such as wash in and wash out patterns of lesion enhancement in addition to the conventional lesion delayed enhancement profile.

The pharmaceutical preparations of the present invention have been demonstrated to provide a sustained vascular enhancement (which may act as a surrogate marker of detecting vascular lesion in different phases). The improved relative vascular intensity performance facilitates simultaneous assessment of both vascular and delayed enhancement of liver lesions with a similar or even reduced gadolinium burden to patients compared with known protocols.

DETAILED DESCRIPTION OF THE PREFERRED EMBODIMENTS

Figure 1:
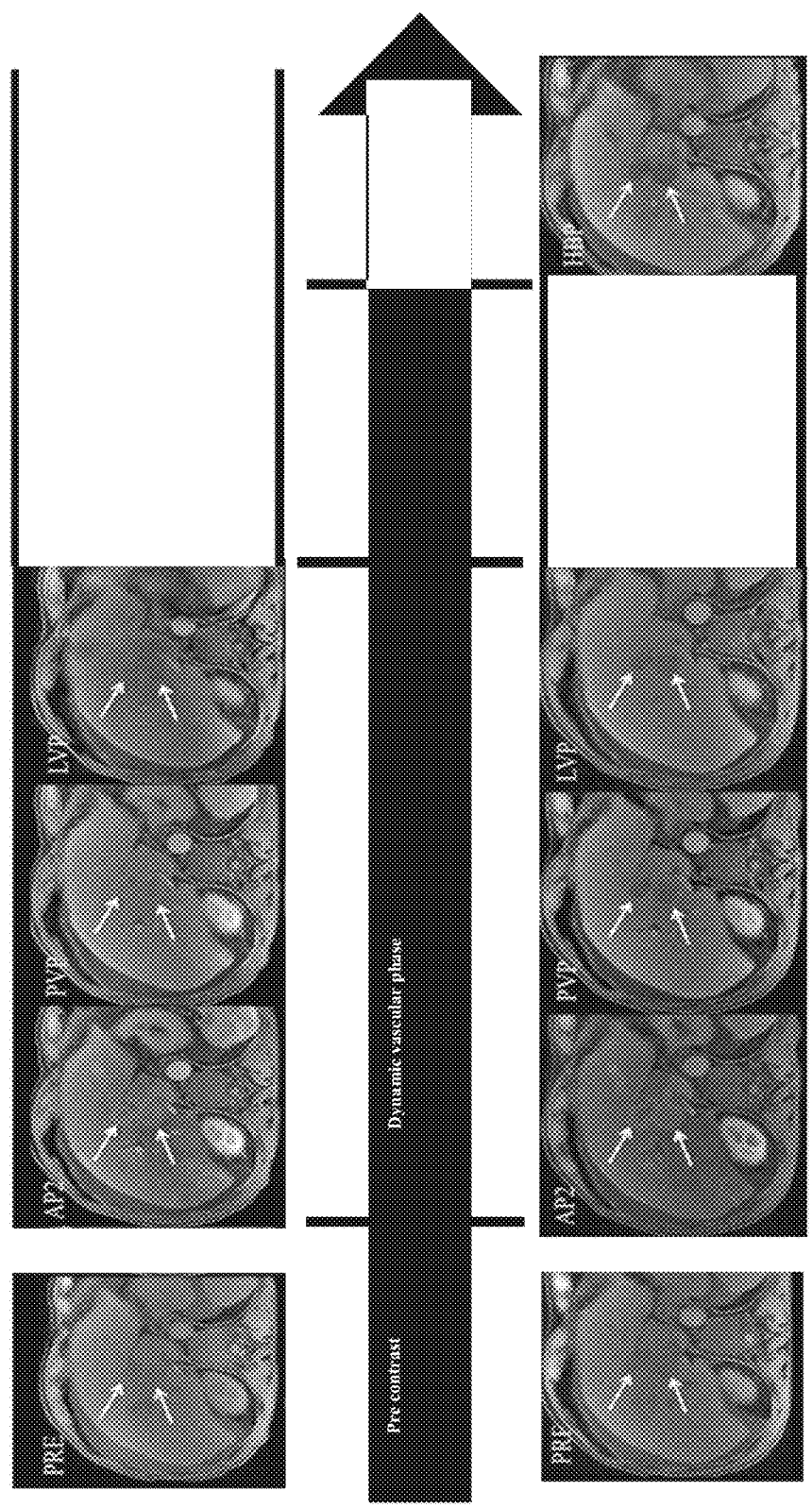
FIG. 1 illustrates examples of the images obtained in a MRI procedure using a first API (bottom) and a second API (top) of the present invention.

To more clearly and concisely describe and point out the subject matter of the claimed invention, definitions are provided hereinbelow for specific terms used throughout the present specification and claims. Any exemplification of specific terms herein should be considered as a non-limiting example.

The terms "comprising" or "comprises" have their conventional meaning throughout this application and imply that the agent or composition must have the essential features or components listed, but that others may be present in addition. The term 'comprising' includes as a preferred subset "consisting essentially of" which means that the composition has the components listed without other features or components being present.

In a first embodiment the present invention provides a pharmaceutical preparation. The term "pharmaceutical preparation" is taken to mean any pharmaceutically-acceptable preparation comprising the first API and the second API as defined herein that permits their simultaneous administration.

The term "active pharmaceutical ingredient" can be understood to mean is that ingredient in a pharmaceutical preparation that is biologically active. In the context of the present invention the term "biologically active" should be understood to mean for the purposes of in vivo imaging rather than as a therapeutic agent.

Following administration, both the first API and the second API of the present invention rapidly equilibrate in the intravascular and interstitial fluid compartments during what is typically referred to as the "dynamic vascular phase" (can also be referred to as the "extracellular phase"). The dynamic vascular phase can be understood to sequentially include the arterial phase (AP), the portal venous phase (PVP) and the late venous phase (LVP). In the case of the first API of the present invention, it also demonstrates "hepatocellular uptake and biliary excretion", which is to say that following the dynamic vascular phase the API is taken up by hepatocytes and the cleared via the hepatobiliary system. In one embodiment, this hepatocellular uptake and biliary excretion represents a significant proportion of the clearance of said first API. In one embodiment the proportion of hepatobiliary clearance of said first API is >10%, in another embodiment >20%, in a further embodiment >30%, and in a yet further embodiment >40%. In one embodiment the proportion of hepatobiliary clearance of said first API is between 10-50%, in another embodiment between 20-50%, in a further embodiment between 30-50% and in a yet further embodiment between 40-50%. The first API has a relatively poor dynamic vascular phase compared with the second API and in particular does not demonstrate what is termed "sustained vascular enhancement", which is to say enhancement continuing into the PVP and LVP. In some embodiments the first API may have a complete or near complete absence of enhancement in the PVP and LVP, known as an "enhancement defect". The second API on the other hand does not have this level of hepatocellular uptake and biliary excretion but rather is primarily excreted via the kidneys following the dynamic vascular phase, i.e. it has a "renal excretion". In one embodiment this renal excretion of said second API can be regarded as a dedicated renal excretion, which is to say that the proportion of hepatobiliary clearance of said second API is negligible. In one embodiment the proportion of said second API cleared by hepatobiliary clearance is no more than 10%. In one embodiment the proportion of said second API cleared by hepatobiliary clearance is no more than 5%.

The term "metal chelate" in the context of the present invention is taken to mean a coordination complex wherein a paramagnetic metal ion is bonded to a surrounding array of molecules or anions comprised in a chelant. A "chelant" is defined herein as an organic compound capable of forming coordinate bonds with a paramagnetic metal ion through two or more donor atoms. In a typical chelant suitable for the present invention 2-6, and preferably 2-4, metal donor atoms are arranged such that 5- or 6-membered rings result (by having a non-coordinating backbone of either carbon atoms or non-coordinating heteroatoms linking the metal donor atoms). Examples of donor atom types which bind well to paramagnetic metal ions as part of chelating agents are: amines, thiols, amides, oximes, and phosphines. It is strongly preferred that the metal chelate of the present invention is "resistant to transchelation", i.e. does not readily undergo ligand exchange with other potentially competing ligands for the metal coordination sites. Potentially competing ligands include the metal chelate itself plus other excipients in the preparation, or endogenous compounds in vivo.

A "paramagnetic metal ion" has unpaired electrons that behave as molecular magnetic dipole moments. The local magnetic field of a paramagnetic metal ion reduces the T1 and T2 relaxation times of surrounding hydrogen nuclei due to dipolar interactions between the paramagnetic ions and the hydrogens.

The "ratio of said first API to said second API" refers to the relative amounts of each of said first API to said second API present in said pharmaceutical preparation. In one embodiment the amount of each of said first API to said second API is defined as a molar amount.

Paramagnetic metal ions suitable for use in MRI are well-known to those of skill in the art as taught for example by Schouman-Claeys and Frija in the chapter "Contrast media" in "MRI of the Body" (2012 Springer Berlin Heidelberg; Daniel Vanel & Michael T. McNamara, Eds.). In one embodiment of the invention said paramagnetic metal ion is a transition metal or a lanthanide. In another embodiment of the invention said paramagnetic metal ion is selected from the group comprising Eu, Gd, Dy, Ho, Cr, Mn and Fe. In a further embodiment of the invention said paramagnetic metal ion is selected from the group comprising Gd, Mn, Fe and Cr. In a yet further embodiment of the invention said paramagnetic metal ion is selected from the group comprising Gd(III) and Mn(II). In a still further embodiment of the invention said paramagnetic metal ion is Gd(III).

For use in MRI, paramagnetic metal ions are administered as metal chelates in order to avoid any toxic effects of these metal ions in their free form. As well as the paramagnetic metal ion being stably complexed, the geometry of the chelant should be such that the paramagnetic effectiveness of the metal ion is maintained. In one embodiment the chelant is any ligand capable of producing a highly stable metal chelate complex, e.g. one with a thermodynamic stability constant of at least $10^{12}$. In various embodiments the chelant can be a linear, cyclic or branched chelating agent, e.g. a linear mono- or polychelant, a macrocyclic chelant or a branched polychelant (e.g. a dendrimeric polychelant). In one embodiment the chelant will be a polyaminopolyoxyacid (e.g. polyaminopolycarboxylic acid). Examples are suitable chelants are described in the art, such as one of the mono and polychelants suggested for lanthanide chelation taught in the patent publications of Nycomed (including Nycomed Imaging and Nycomed Salutar), Sterling Winthrop, Schering, Bracco, Squibb, Mallinckrodt, Guerbet and Metasyn, e.g. U.S. Pat. No. 4,647,447, EP0071564-A, WO1996003154, WO1996001655, EP0430863-A, WO1996041830, WO1993010824, WO1989000557, EP0292689-A, EP0232751-A, EP0230893-A, EP0255471-A, EP0277088-A, EP0287465-A. U.S. Pat. No. 5,334,371 discloses macrocyclic polyaza bicyclo compounds containing Mn(II) ions. WO2011073371 (GE Healthcare AS) discloses chelants optimized for chelation of Mn(II) that are kinetically stable and show optimal water exchange kinetics. WO2011121002 and US20140086846 (General Electric Company) teach chelant structures optimized for chelation of transition metals and in particular iron. DTPA-bisalkylamides and methods for their preparation are disclosed in U.S. Pat. No. 4,687,659 and DTPA-bis(hydroxyalkyl-amides) and methods for their preparation are disclosed in U.S. Pat. No. 4,826,673 and EP-A-130934. WO2009103744, WO2016083597, WO2016083605 and WO2016083600 all describe methods to obtain gadolinium-based MRI contrast agents consisting of a DOTA chelant and gadolinium ($Gd^{3+}$). In one embodiment of the pharmaceutical preparation of the invention said chelant is selected from the group comprising: diethylenetriaminepentaacetic acid (DTPA); 4-carboxy-5,8,11-tris(carboxymethyl)-1-phenyl-2oxa-5,8,11-triazatridecan-13-oic acid (BOPTA); 1,4,7,10-tetraazacyclododecan-1,4,7-triactetic acid (DO3A); 1,4,7,10-tetraazacyclododecan-1,4,7,10-tetraactetic acid (DOTA); ethylenediaminotetraacetic acid (EDTA); 10-(2-hydroxypropyl)-1,4,7,10-tetraazacyclododecan-1,4,7-triacetic acid (HP-DO3A); 2-methyl-1,4,7,10-tetraazacyclododecan-1,4,7,10-tetraacetic acid (MCTA); tetramethyl-1,4,7,10-tetraazacyclododecan-1,4,7,10-tetraacetic acid (DOTMA); 3,6,9,15-tetraazabicyclo[9.3.1]pentadeca-1(15),11,13-triene-3,6,9-triacetic acid (PCTA); N,N'Bis(2-aminoethyl)-1,2-ethanediamine (TETA); 1,4,7,10-tetraazacyclotridecane-N,N',N'',N'''-tetraacetic acid (TRITA); 1,12-dicarbonyl, 15-(4-isothiocyanatobenzyl) 1,4,7,10,13-pentaazacyclohexadecane-N,N',N'' triaceticacid (HETA); [(2S,5S,8S,11S)-4,7-bis-carboxymethyl-2,5,8,11-tetramethyl-1,4,7,10-tetraazacyclo-dodecan-1-yl]acetic acid, (M4DO3A); 1-O-Phosphonomethyl-1,4,7,1-O-tetraazacyclododecane-1,4,7-triacetic acid (MPDO3A); hydroxybenzyl-ethylenediamine-diacetic acid (HBED); N,N'-ethylenebis-[2-(o-hydroxyphenolic)glycine](EHPG); 10-[(1SR,2RS)-2,3-dihydroxy-1-hydroxymethylpropyl]-1,4,7,10-tetraazacyclododecane-1,4,7-triacetic acid (BT-DO3A); and, 2-[bis[2-[carboxylatomethyl-[2-(2-methoxyethylamino)-2-oxoethyl]amino]ethyl]amino]acetate (DTPA-BMEA).

A "derivative" of a chelant is to be understood in the context of the present invention as the chelant comprising a further chemical group that does not interfere with the chelating properties of the chelant. Such a chemical group may be included in order to functionalise the metal chelate with a biological targeting moiety or to adjust the pharmacokinetic properties of the metal chelate. Non-limiting examples of chelant derivatives include: DTPA derivatives such as N-[2-[bis(carboxymethyl)amino]-3-(4-ethoxyphenyl)propyl]-N-[2-[bis(carboxymethyl)-amino]ethyl]-L-glycine (EOB-DTPA), N,N-bis[2-[bis(carboxymethyl)amino]-ethyl]-L-glutamic acid (DTPA-Glu), N,N-bis[2-[bis(carboxymethyl)amino]-ethyl]-L-lysine (DTPA-Lys), N,N-bis[2-[carboxymethyl[(methylcarbamoyl)methyl]amino]-ethyl] glycine (DTPA-BMA); DOTA derivatives such as 1,4,7,10-tetraazacyclododecane-N,N',N'',N'''-tetraacetic acid mono-(N-hydroxysuccinimidyl) ester (DOTA-NHS) and [(2S,5S, 8S, 11S)-4,7,10-tris-carboxymethyl-2,5,8,11-tetramethyl-1,4,7,10-tetraazacyclododecan-1-yl]acetic acid (M4DOTA); DOTMA derivatives such as (R)-2-[(2S,5S,8S,11S)-4,7,10-tris-((R)-1-carboxyethyl)-2,5,8,11-tetramethyl-1,4,7,10-tetraazacyclododecan-1-yl]propionic acid (M4DOTMA); PCTA derivatives such as PCTA12 and cyclo-PCTA12; and TETA derivatives such as N,N'-Bis(2-aminoethyl)-1,2-ethanediamine-N-hydroxy-succinimide ester (TETA-NHS).

In a further embodiment of the pharmaceutical preparation of the invention said chelant is selected from DTPA, DOTA or derivatives thereof. In a yet further embodiment of the pharmaceutical preparation of the invention said chelant or derivative thereof is selected from EOB-DTPA, DTPA-BMA, DTPA-BMEA, DTPA, DOTA, BOPTA, HP-DO3A and BT-DO3A.

Each of the first API and second API may be prepared by methods well known to those of skill in the art by reacting a suitable chelant and a suitable paramagnetic metal together. The reaction is typically performed in an aqueous solution, e.g. in distilled water optionally containing a miscible co-solvent, at an elevated temperature, e.g. 70 to 95° C., preferably 80-90° C. During the reaction the pH is generally 3 to 6 and may be controlled by addition of an acid or base, for example an acid or base which produces pharmaceutically acceptable neutralisation products, such as hydrochloric acid and sodium hydroxide. The progress of the reaction will generally be monitored to determine the residual quantities of unreacted chelant or paramagnetic metal ion, with extra portions optionally being added until the reaction is deemed to be complete, e.g. when a stable low concentration of chelant and negligible free paramagnetic metal ion is detected. Typically thereafter the reaction mixture is cooled, e.g. to below 25° C. If necessary the pH of the reaction mixture is then adjusted, e.g. to about 6, for example using sodium hydroxide. The solution is then filtered and the metal chelate is isolated using methods well-known to the skilled person, e.g. by crystallisation chromatography, and the like and thereafter admixed with a biocompatible carrier and one or more excipients as defined herein. In one embodiment of the pharmaceutical preparation of the invention the ratio of said first API to said second API is from 1:5 to 3:2. In another embodiment said ratio is from 1:4 to 1:1. In a further embodiment said ratio is 1:1. In a yet further embodiment said ratio is 1:2. In a still further embodiment said ratio is 1:3. In a still further embodiment said ratio is 1:4.

The combined API dose of the present invention should not exceed the recommendations for a single API dose. In certain embodiments the total cumulative dose is less than or equal to 0.125 mmol/kg.

The chemical structures are provided in the table below of certain known APIs and the commercially-available MRI pharmaceutical preparations in which they are formulated (note that counter ions, if present, are omitted from the chemical structures):

| Product Name (Chemical Name) | Chemical Structure |
| --- | --- |
| Omniscan (gadodiamide) | 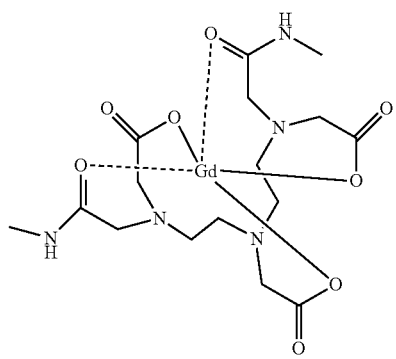 |
| Optimark (gadoversetamide) | 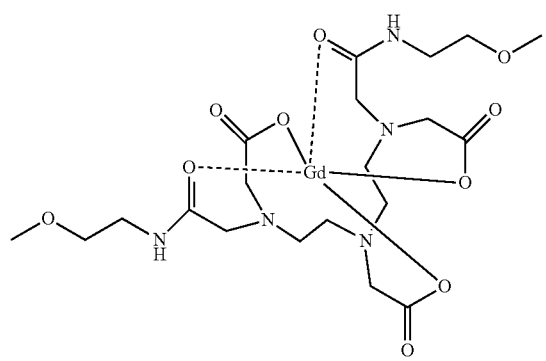 |
| Magnevist (gadopentate dimeglumine) | 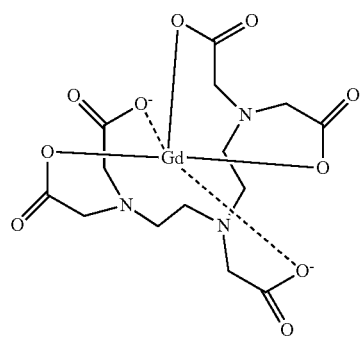 |
| ProHance (gadoteridol) | 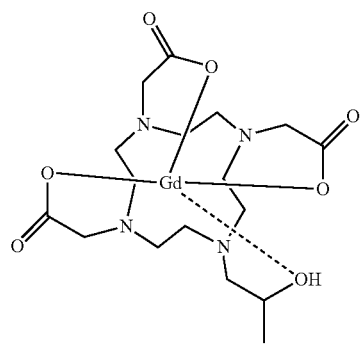 |

-continued
| Product Name (Chemical Name) | Chemical Structure |
|---|---|
| Gadavist (gadobutrol) | 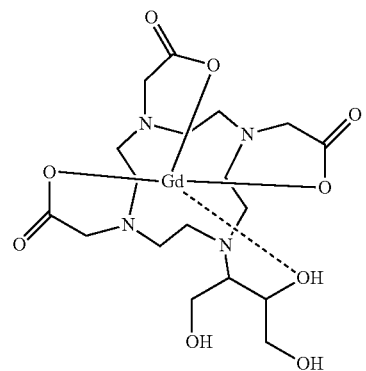 |
| MultiHance (gadobenate dimeglumine) | 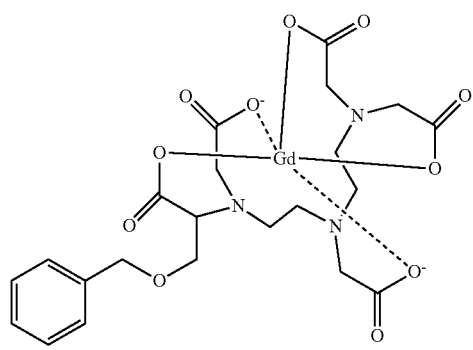 |
| Eovist (gadoxetate disodium) | 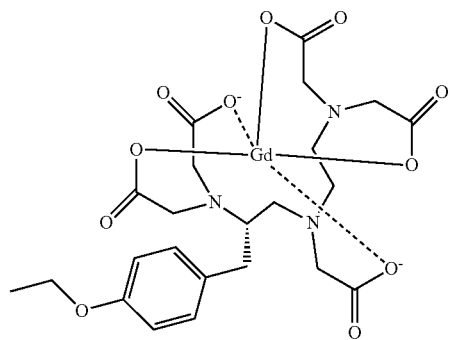 |

| Product Name (Chemical Name) | Chemical Structure |
|---|---|
| Ablavar (gadofosveset trisodium) | 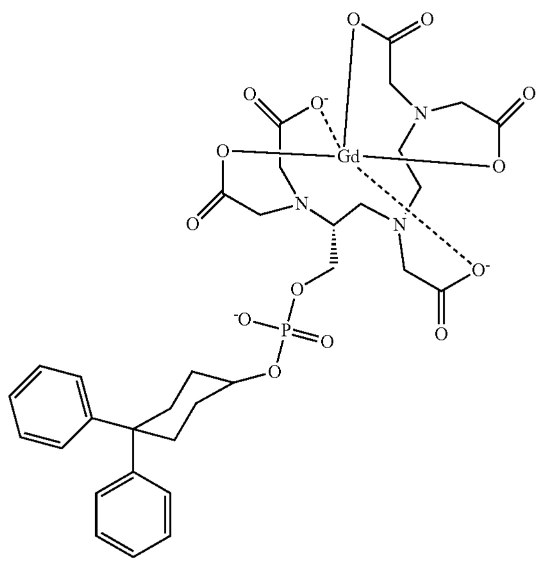 |
| Dotarem (gadoterate meglumine) | 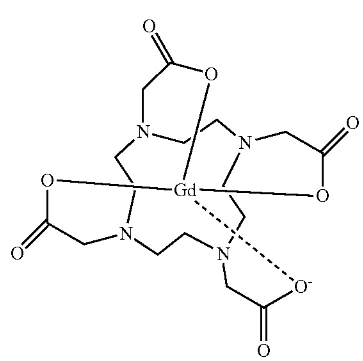 |

In one embodiment of the pharmaceutical preparation of the invention said first API is gadoexetate.

In one embodiment of the pharmaceutical preparation of the invention said second API is selected from the group comprising gadodiamide, gadoversetamide, gadopentate, gadoteridol, gadobutrol, gadobenate, gadofosveset and gadoterate. In another embodiment, said second API is selected from the list comprising gadoteridol, gadobutrol and gadoterate. In a further embodiment, said second API is selected from gadobutrol and gadoterate.

Gadoxetate has up to 50% hepatobiliary excretion in the normal liver. After intravenous injection, gadoxetate distributes into the vascular and extravascular spaces during the dynamic vascular phase and progressively into the hepatocytes and bile ducts during the hepatobiliary phase. Gadoxetate adds substantial information during the hepatobiliary phase, improving the detection and characterization of focal liver lesions and diffuse liver disease (Beers 2012 J Hepatol; 57 (2): 421-429).

FIG. 1 shows MR images of a human liver obtained over time using non-limiting examples of a first API (bottom=gadoxetate) and a second API (top=gadoterate).

The "pre" image (sometimes referred to as "pre-contrast image") is acquired prior to arrival of any API in the image. The "dynamic" image (sometimes referred to as "dynamic contrast-enhanced MRI") is acquired immediately after the arrival of any API in the image. The "delayed" image (sometimes referred to as "delayed contrast-enhanced MRI") is acquired at a time point after the arrival of any API in the image. For the three distinct phases of the dynamic vascularphase: in AP, the API has been delivered mainly through the hepatic artery; in PVP, the API in the liver has been delivered also through the inferior vena cava and portal vein; and in the LVP the second API is distributed mainly extracellularly. The "HBP" (hepatobiliary phase) image is acquired at a time point when the first API has had sufficient time to accumulate in the hepatocytes to allow acquisition with good contrast-to-noise.

In one embodiment of the pharmaceutical preparation of the invention said first API and said second API are provided separately but configured to permit simultaneous administration. For example, it is envisaged that the two APIs may be provided in separate syringes that are placed in an apparatus (injector) capable of injecting the two syringes at the same time, with individual rate and dosing control. The two APIs are therefore mixed upon leaving the individual syringes, before entering the patient. In an alternative embodiment, the two APIs may be placed in a double barrel syringe so as to be separated until the point of injection. In a further embodiment, the two APIs may be provided in one syringe, separated by a membrane that is pierced upon injection allowing for mixing upon injection.

In one embodiment of the pharmaceutical preparation of the invention each of said first API and said second API are provided as a pharmaceutical composition together with a biocompatible carrier.

The "biocompatible carrier" is a fluid, especially a liquid, in which the first API or the second API is (or both APIs together are) suspended or dissolved, such that the resulting composition is physiologically tolerable, i.e. can be administered to the mammalian body without toxicity or undue discomfort (which can be understood to be a definition of the term "suitable for mammalian administration").

In an alternative embodiment the pharmaceutical preparation of the invention is provided as a pharmaceutical composition wherein said first API and said second API are formulated together with a biocompatible carrier. For this embodiment, the two APIs may be premixed and distributed as a new formulation containing optimal proportions of the first API and the second API as defined herein.

In one embodiment the pharmaceutical composition of the invention may comprise one or more pharmaceutically acceptable excipients. Non-limiting examples of suitable pharmaceutically acceptable excipients include buffering agents, stabilizers, antioxidants, osmolality adjusting agents, buffers, pH adjusting agents, excess chelant, weak complexes of physiologically tolerable ions such as calcium chelates, calcium or sodium salts like calcium chloride, calcium ascorbate, calcium gluconate or calcium lactate. These and other suitable excipients will be well known to those of skill in the art and are further described in e.g. WO1990003804, EP0463644-A, EP0258616-A and U.S. Pat. No. 5,876,695 the content of which are incorporated herein by reference. The pharmaceutical composition of the invention in one embodiment is in a form suitable for parenteral administration, for example injection. Thus the APIs of the present invention may be in conventional pharmaceutical administration forms such as solutions, suspensions and dispersions in physiologically acceptable carrier media, for example water for injections. The pharmaceutical composition according to the invention may therefore be formulated for administration using physiologically acceptable excipients in a manner fully within the skill of the art. For example, the APIs, optionally with the addition of pharmaceutically acceptable excipients, may be suspended or dissolved either separately or together in an aqueous medium, with the resulting solution or suspension then being sterilized. Non-limiting examples of pharmaceutically acceptable excipients include, for example, physiologically biocompatible buffers (as for example, tromethamine hydrochloride), slight additions of other chelants (as for example, diethylenetriaminepentaacetic acid) or, optionally, calcium or sodium salts (for example, calcium chloride, calcium ascorbate, calcium gluconate or calcium lactate). For MRI procedures the typical mode of administration is parenteral, e.g. intravenous, administration. Parenterally administrable forms, e.g. intravenous solutions, should be sterile and free from physiologically unacceptable agents and should have low osmolality to minimize irritation or other adverse effects upon administration and thus the pharmaceutical composition should be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, $22^{nd}$ Edition (2006 Lippincott Williams & Wilkins) and The National Formulary (https://books.google.com/books?id=O3qix-PEMwssC&q=THE+NATIONAL+FORMULARY&dq= THE+NATIONAL+FORMULARY&hl=en&sa=X&ved= 0CC8Q6AEwAGoVChMImfPHrdTqyAIVJfNyCh1RJw_ E). The pharmaceutical compositions can also contain preservatives, antimicrobial agents, buffers and antioxidants conventionally used in parenteral solutions, and other excipients compatible with the chelants and related metal chelates and which will not interfere with the manufacture, storage or use of the final products.

In one embodiment each of the first API and the second API comprises a charge-balancing counterion, which may be an organic cation or an inorganic cation. Thus, in one embodiment, the charge balancing counterion is an inorganic cation. Non-limiting examples of inorganic cations include alkali metal cations, alkaline earth metal cations, transition metal cations, and inorganic ammonium cations ($NH_4^+$). In another embodiment, the charge balancing counterion is an organic cation, for example an organic ammonium cation, an organic phosphonium cation, an organic sulfonium cation, or a mixture thereof. In one embodiment, the charge balancing counterion is the ammonium salt of an aminosugar such as the 2-(N,N,N-trimethylammonium)-2-deoxyglucose. In one embodiment, the charge balancing counterion is the protonated form of N-methyl glucamine.

Methods for the preparation of a pharmaceutical composition are well known in the art. For preparation of a pharmaceutical composition comprising the first API and the second API together with a biocompatible carrier, the metal chelates may be prepared separately and then admixed in the desired ratio. For the pharmaceutical composition to be administered parenterally, i.e. by injection its preparation further comprises steps including removal of organic solvent, addition of a biocompatible buffer and any optional further ingredients such as excipients or buffers. For parenteral administration, steps to ensure that the pharmaceutical composition is sterile and apyrogenic also need to be taken.

In one embodiment where the first API and the second API are present in the same pharmaceutical composition it is specifically formulated to reduce the risk of precipitation and transmetallation. In one embodiment the choice of buffer can act to eliminate the risk of precipitation of salt forms of the APIs. In one embodiment, the addition of excess chelant can act to stabilise the composition to avoid transmetallation. In one embodiment of the pharmaceutical preparation of the invention gadoexetate and gadoterate meglumine are formulated together with an excess of the free acid of EOB-DTPA, and wherein meglumine is a sole buffering agent. The relative composition of gadoexetate and gadoterate meglumine can be determined from imaging efficacy. In another embodiment this pharmaceutical preparation with gadoexetate and gadoterate meglumine comprises megluminium instead of calcium and sodium ions, which eliminates the risk of precipitation of the sodium salt of gadoterate. This embodiment is further advantageous in that the formulation is simplified since the buffering agent commonly used in gadoexetate formulations, trometamol, is not included. The chemical composition of this embodiment is illustrated below:

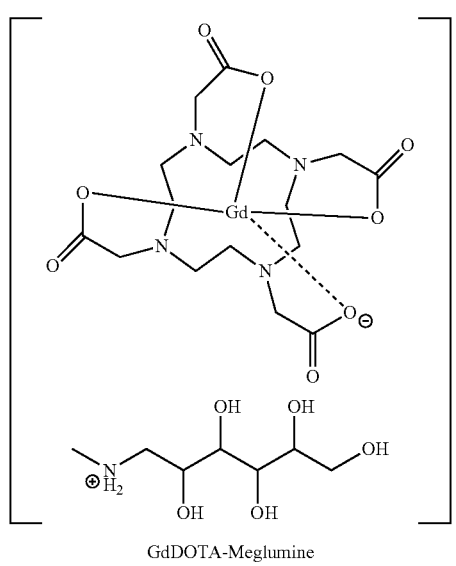

GdDOTA-Meglumine

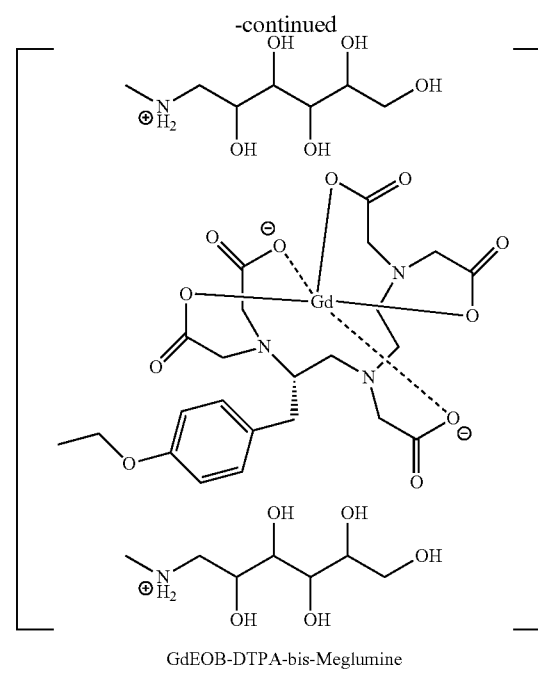

GdEOB-DTPA-bis-Meglumine

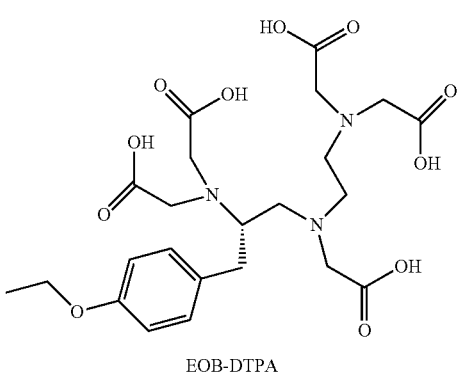 [SMILES: CCOc1ccc(C[C@@H](CN(CCN(CC(=O)O)CC(=O)O)CC(=O)O)N(CC(=O)O)CC(=O)O)cc1]

EOB-DTPA

The above formulation could be obtained by mixing commercially available liquid bulk of gadoterate meglumine with Gd-EOB-DTPA-bis-megluminium salt/solution as shown in the scheme below.

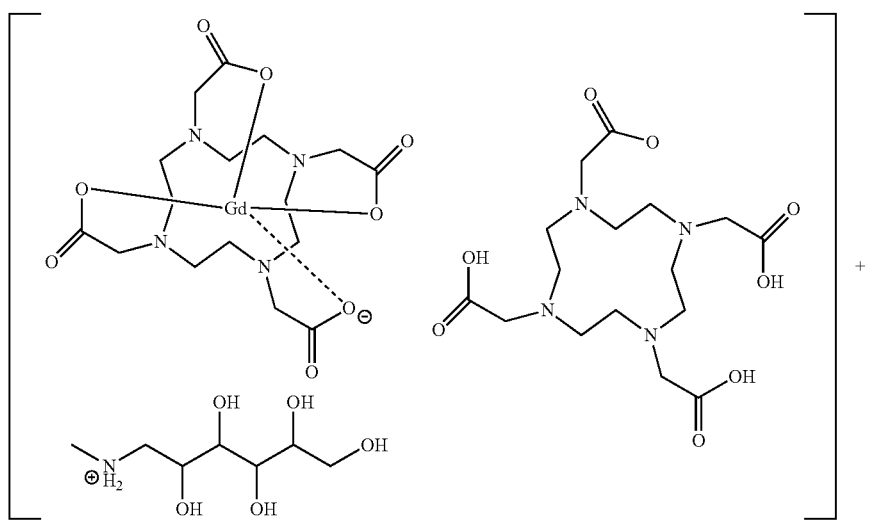
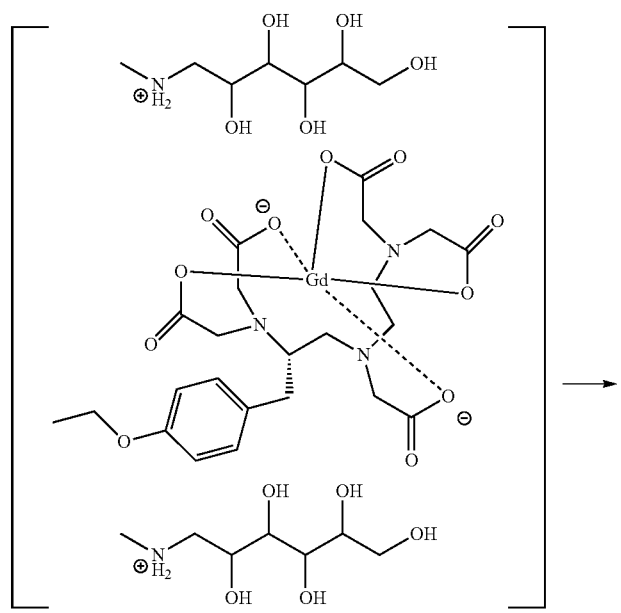
In another embodiment a process can be used that utilizes commercially available DOTA and chelant EOB-DTPA in an in situ complexation reaction, where gadolinium oxide is added to DOTA/EOB-DTPA ligand mixture and the proportion of excess free ligand (EOB-DTPA) is set by a measure and adjust step (as described e.g. in EP2242515-B1) prior to pH adjustment with meglumine.

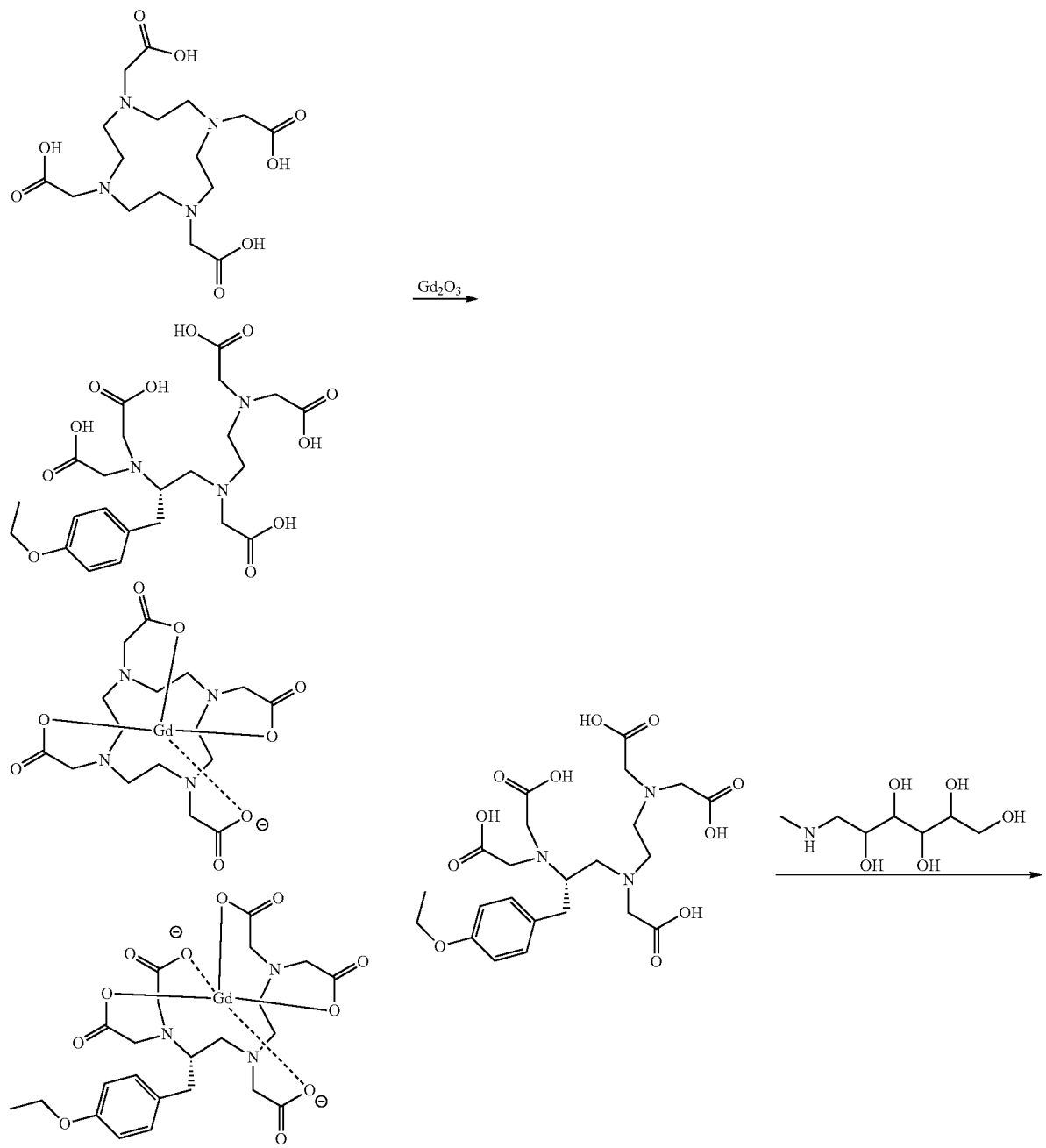

It is known that there is a correlation between the amount of excess chelant in a Gd chelate formulation and the amount of Gd deposited in animal models (Sieber 2008 J Mag Res Imaging; 27 (5): 955-62). Therefore, in another embodiment where the first API and the second API are formulated together and at least one of said first API and said second API comprise Gd, an amount of excess chelant is selected that can act as a Gd scavenger so as to reduce or prevent release of Gd from the formulation post injection. The optimal amount of free chelant will result in a pharmaceutical composition having suitable physicochemical properties (i.e. viscosity, solubility and osmolality) and avoiding toxological effects such as zinc depletion in the case of too much free chelant.

In a second embodiment the pharmaceutical preparation of the present invention is provided as a dose to be administered to a subject.

In the present invention the term "dose" is taken to mean a measured quantity of the pharmaceutical preparation as defined herein to be administered to a subject at one time for the purposes of an MRI procedure.

The "subject" can be any human or animal subject. In one embodiment the subject is a mammal, i.e. an intact mammalian body in vivo. In one embodiment the subject is a living human or non-human animal body.

In one embodiment of the dose of the invention the combined dose of said first API and second API is less than 0.125 mmol per kilogram of said subject.

In one embodiment the dose of the invention comprises between 0.02-0.03 mmol per kilogram of said subject of said first API.

In the dose of the present invention the ratios can be modified as the dynamic contribution from the first API can be harnessed during the dynamic phase of the second API. In certain embodiments this allows for a reduction of contrast agent dose, while maintaining sufficient enhanced arterial phase (in combination with the signal contribution from the first API).

Figure 2:
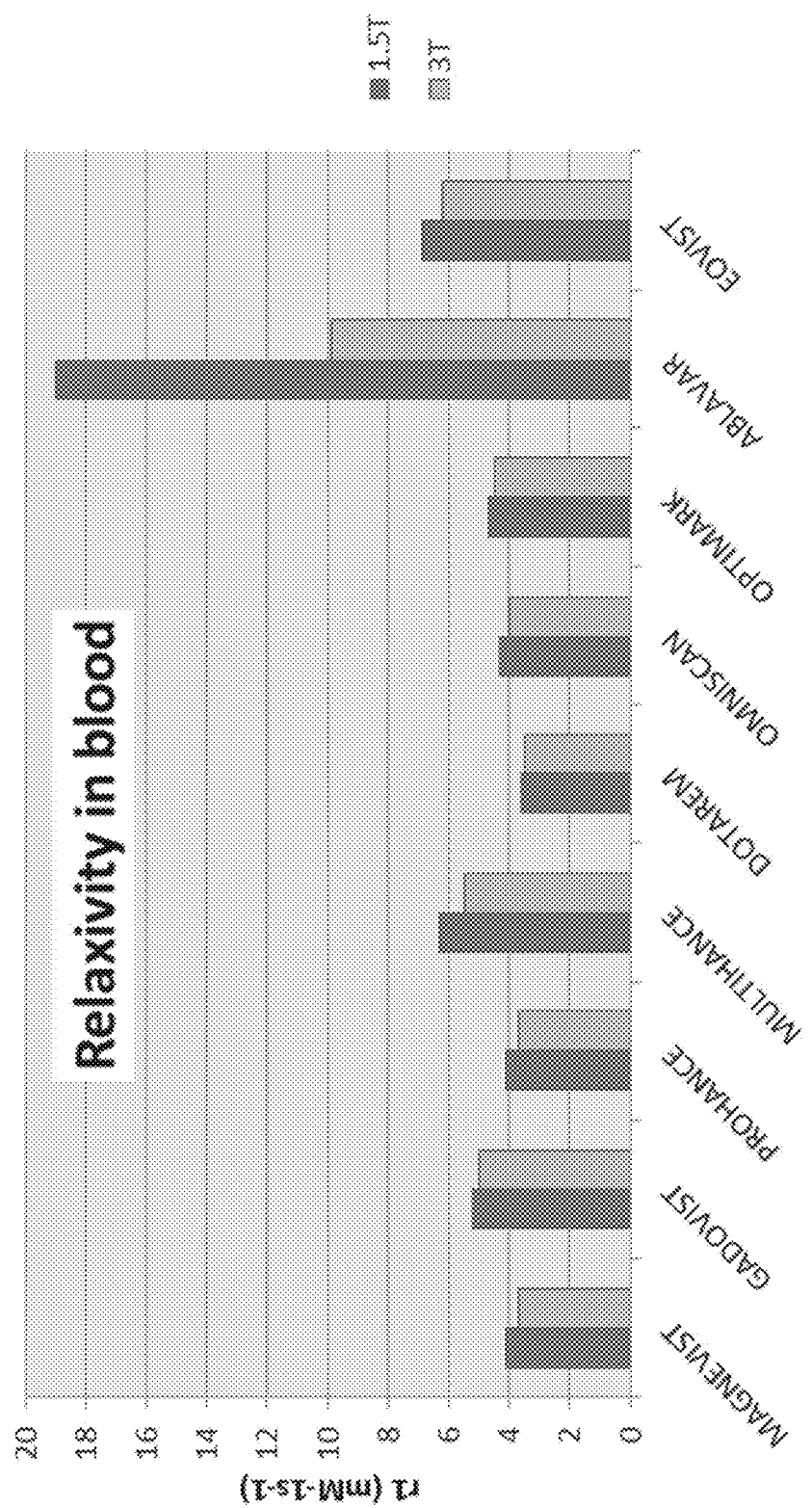
FIG. 2 shows the relaxivity values of a number of commercially-available MRI agents.

In certain embodiments of the present invention the absolute quantities and relative amounts of each of said first API and said second API are determined based on the relaxivity of said second API. The concept of "relaxivity" of an MRI agent is well known to those of skill in the art and refers to the ability of magnetic compounds to increase the relaxation rates of the surrounding water proton spins. Relaxivity is used to improve the contrast of an MR image, and to study tissue specific areas where the contrast agent better diffuses or to perform functional MRI. The relaxivity of MRI agents depends on the molecular structure and kinetic of the complex. Relaxivity depends on the temperature, field strength, and substance in which the contrast agent is dissolved. In the context of the present invention the conditions for which the relaxivity values have been set are in vivo at 37° C. (as opposed to e.g. in water at ambient temperatures of ~20° C.). The relaxivities of 8 commonly-used Gd-based MRI agents have been described by Shen et al (2015 Invest Radiol; 50 (5): 330-8). FIG. 2 illustrates the relaxivity values in blood of a number of known MRI agents at 1.5 T and 3 T.

In one embodiment the dose of the invention comprises between 0.025-0.1 mmol per kilogram of said subject of said second API wherein said second API has a relaxivity ≥3 mM−1 s−1 at field strengths of 1.5-3. The value ≥3 mM−1 s−1 can in one embodiment be regarded as encompassing 3-5 mM−1 s−1, in another embodiment 3-4 mM−1 s−1, in a further embodiment 4-5 mM−1 s−1 and in a yet further embodiment 3.5 mM−1 s−1. In certain embodiments a dose in accordance with the embodiments of this paragraph is selected from:

0.02 mmol per kilogram of said subject of said first API and between 0.04-0.1 mmol per kilogram of said subject of said second API; or, 0.02 mmol per kilogram of said subject of said first API and between 0.05-0.1 mmol per kilogram of said subject of said second API; or, 0.025 mmol per kilogram of said subject of said first API and between 0.03-0.1 mmol per kilogram of said subject of said second API; or, 0.025 mmol per kilogram of said subject of said first API and between 0.04-0.1 mmol per kilogram of said subject of said second API; or, 0.025 mmol per kilogram of said subject of said first API and 0.1 mmol per kilogram of said subject of said second API; or, 0.025 mmol per kilogram of said subject of said first API and 0.05 mmol per kilogram of said subject of said second API; or, 0.03 mmol per kilogram of said subject of said first API and between 0.025-0.1 mmol per kilogram of said subject of said second API; or, 0.03 mmol per kilogram of said subject of said first API and between 0.04-0.095 mmol per kilogram of said subject of said second API.

In one embodiment the dose of the invention comprises between 0.02-0.09 mmol per kilogram of said subject of said second API wherein said second API has a relaxivity ≥5 mM−1 s−1 at field strengths of 1.5-3 T. The value ≥5 mM−1 s−1 can in one embodiment be regarded as encompassing 5-7 mM−1 s−1 and in another embodiment 5-6 mM−1 s−1. In certain embodiments a dose in accordance with the embodiments of this paragraph is selected from:

0.02 mmol per kilogram of said subject of said first API and between 0.03-0.09 mmol per kilogram of said subject of said second API; or, 0.02 mmol per kilogram of said subject of said first API and between 0.04-0.09 mmol per kilogram of said subject of said second API; or, 0.025 mmol per kilogram of said subject of said first API and between 0.025-0.09 mmol per kilogram of said subject of said second API; or, 0.025 mmol per kilogram of said subject of said first API and between 0.03-0.08 mmol per kilogram of said subject of said second API; or, 0.025 mmol per kilogram of said subject of said first API and 0.05 mmol per kilogram of said subject of said second API; or, 0.03 mmol per kilogram of said subject of said first API and between 0.02-0.09 mmol per kilogram of said subject of said second API; or, 0.03 mmol per kilogram of said subject of said first API and between 0.03-0.075 mmol per kilogram of said subject of said second API.

In one embodiment the dose of the invention comprises between 0.02-0.07 mmol per kilogram of said subject of said second API wherein said second API has a relaxivity ≥7 mM−1 s−1 and field strengths of 1.5-3 T. The value ≥7 mM−1 s−1 can in one embodiment be regarded as encompassing ≥8 mM−1 s−1 and in another embodiment 8-9 mM−1 s−1. In certain embodiments a dose in accordance with the embodiments of this paragraph is selected from:

0.02 mmol per kilogram of said subject of said first API and between 0.02-0.07 mmol per kilogram of said subject of said second API; or, 0.02 mmol per kilogram of said subject of said first API and between 0.03-0.06 mmol per kilogram of said subject of said second API; or, 0.025 mmol per kilogram of said subject of said first API and between 0.02-0.07 mmol per kilogram of said subject of said second API; or, 0.025 mmol per kilogram of said subject of said first API and between 0.025-0.06 mmol per kilogram of said subject of said second API; or, 0.03 mmol per kilogram of said subject of said first API and between 0.02-0.06 mmol per kilogram of said subject of said second API.

In one embodiment the dose of the invention comprises between 0.01-0.06 mmol per kilogram of said subject of said second API wherein said second API has a relaxivity ≥9 mM−1 s−1 at field strengths of 1.5-3 T. The value ≥9 mM−1 s−1 can in one embodiment be regarded as encompassing 9-11 mM−1 s−1 and in another embodiment 10 mM−1 s−1. In certain embodiments a dose in accordance with the embodiments of this paragraph is selected from:

0.02 mmol per kilogram of said subject of said first API and between 0.02-0.06 mmol per kilogram of said subject of said second API; or, 0.02 mmol per kilogram of said subject of said first API and between 0.02-0.05 mmol per kilogram of said subject of said second API; or, 0.025 mmol per kilogram of said subject of said first API and between 0.02-0.06 mmol per kilogram of said subject of said second API; or, 0.025 mmol per kilogram of said subject of said first API and between 0.02-0.05 mmol per kilogram of said subject of said second API; or, 0.03 mmol per kilogram of said subject of said first API and between 0.01-0.05 mmol per kilogram of said subject of said second API.

In a third embodiment the present invention provides an MRI method comprising administration of a dose of the pharmaceutical preparation of the invention as defined herein.

Methods of administering and subjects envisaged as suitable have been described hereinabove in connection with the pharmaceutical composition. The pharmaceutical composition is administered in an amount suitable to enhance the contrast in the method of MR imaging. MRI methods using APIs such as the first API and the second API as described herein are well-known to those of skill in the art, e.g. as taught in Chapter 27 "Contrast Agents and Magnetic Resonance Imaging" in "Magnetic Resonance Imaging: Physical and Biological Principles" (4$^{th}$ Edition 2015 Elsevier, Stewart Carlyle Bushong & Geoffrey Clarke, Eds.) or in "Contrast Agents I: Magnetic Resonance Imaging" (2002 Springer-Verlang, Werner Krause, Ed.).

The method of the invention has utility as a method for diagnosis. The examples herein demonstrate that the method of the invention provides certain advantages that will be useful in the detection and characterization of focal liver lesions and diffuse liver disease compared with known such methods. The present inventors compared the performance of formulations comprising either gadoxetate (an example of a "first API" as defined herein) or gadoterate (an example of a "second API" as defined herein) as the sole API with that of a number of formulations comprising a combination of gadoxetate with either gadoterate or gadobutrol (another example of a "second API" as defined herein). The combination formulations represent embodiments of the pharmaceutical preparation according to the present invention and are referred to the Examples as "Combo" formulations. In the analysis of vascular intensity of the Combo formulations following administration of a dose in vivo, all formulations provided peak % RVI (% relative vascular intensity) at AP with decreased signal at the later PVP and LVP. A significant reduction of % RVI was found at PVP phase with the formulation having gadoxetate as the sole API compared to all other formulations tested (Combo 1, Combo 2, Combo 3 and gadoterate). This trend continued to decrease into LVP, with no vascular enhancement evident from gadoxetate at 120 secs post injection, demonstrating the poor dynamic vascular endurance of this liver specific agent. This enhancement defect in the post-vascular phase has been previously recognised as a pitfall of hepatobiliary agents compared to non-specific gadolinium based contrast (Frydrychowicz et al 2012, JMRI; 35 (3): 492-511). The AUC was significantly increased in all combo test items (Combo 1, Combo 2 and Combo 3) in comparison to gadoxetate (93.8 AU, 76.7 AU, 84.9 AU vs. 34.2 AU) and gadoterate (93.8 AU, 76.7 AU, 84.9 AU vs. 63.2 AU). These results demonstrate that the pharmaceutical preparation of the present invention provides both good early arterial enhancement as well as an improvement in sustained RVI throughout the entire vascular phase. These observations were made for the Combo formulations not only in contrast to a formulation including gadoxetate as the sole API but also in contrast to a formulation including gadoterate as the sole API.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. The entire disclosures of all documents mentioned herein are incorporated herein by reference.

EXAMPLES

List of Abbreviations Used in the Examples

AUC area under the curve
ICP-MS inductively-coupled plasma mass spectrometry
IV intravenous
FoV field of view
IVC inferior vena cava
LAVA Liver Acquisition with Volume Acquisition
MRI magnetic resonance imaging
NEX number of excitations
NMR nuclear magnetic resonance
PAC Port-a-cath
PV intrahepatic portal vein
ROI region of interest
RVI relative vascular intensity
SI signal intensity
TE echo time
TR repetition time
UZB Universitair Ziekenhuis Brussel Test Items The following test items were used to evaluate the present invention:
(i) Gadoxetate (disodium; 2-[[2-[bis(carboxylatomethyl) amino]-3-(4-ethoxyphenyl)propyl]-[2-bis(carboxylatomethyl)amino]ethyl]amino]acetate, gadolinium (3+)) was purchased from Bayer Pharma AG (D-13342 Berlin Germany). The commercially supplied gadoxetate formulation contains 181.43 mg/ml gadoxetate disodium, equivalent to 0.25 mmol/ml, the excipients caloxetate trisodium, trometamol, hydrochloric acid and/or sodium hydroxide (for pH adjustment), and water for injection. For use in these studies, it was diluted in water for injection (BBraun) to a concentration of 0.083 mmol/ml and administered at 0.3 ml/kg to give the final dose (0.025 mmol/kg).
(ii) Gadoterate (2-[4,7-his(carboxylatomethyl)-1 0-(carboxymethyl)-1,4, 7,10-tetrazacyclododec-1-yl]acetate; gadolinium(3+)) was manufactured by GE Healthcare. Gadoterate meglumine contains 279.3 mg/ml gadoterate, equivalent to 0.5 mmol/ml and the excipients meglumine and water for injection. For use in these studies, it was diluted in water for injection (BBraun) to a concentration of 0.333 mmol/ml and administered at 0.3 ml/kg to give the final dose (0.1 mmol/kg).
(iii) Combo 1 is a combination of gadoxetate and gadoterate. Combo 1 was formulated in water for injection (BBraun) to a concentration of 0.083 mmol/ml and 0.333 mmol/ml respectively. Administration of 0.3 ml/kg was given for a final dose of gadoxetate (0.025 mmol/kg) and gadoterate (0.1 mmol/kg).
(iv) Combo 2 is a combination of gadoxetate and gadoterate. Combo 2 was formulated in water for injection (BBraun) to a concentration of 0.083 mmol/ml and 0.167 mmol/ml respectively. Administration of 0.3 ml/kg was given for a final dose gadoxetate (0.025 mmol/kg) and gadoterate (0.05 mmol/kg).

(v) Combo 3 is a combination of gadoxetate and gadobutrol. Gadobutrol (10-(2,3-Dihydroxy-1-hydroxymethylpropyl)-1,4,7,10-tetraazacyclododecane-1,4,7-triacetic acid) was purchased from Bayer Pharma AG (D-13342 Berlin Germany). Gadobutrol commercially supplied formulation contains 604.72 mg/ml gadobutrol, (equivalent to 1.0 mmol/ml) and water for injection. For use in these studies, it was diluted in water for injection (BBraun) to a concentration of 0.333 mmol/ml (equal molar concentration to gadoterate). The diluted gadobutrol solution was used for the preparation of Combo 3. Combo 3 was formulated in water for injection (BBraun) to a concentration of 0.083 mmol/ml for gadoxetate and 0.167 mmol/ml for gadobutrol. Administration of 0.3 ml/kg was given for a final dose of gadoxetate (0.025 mmol/kg) and gadobutrol (0.05 mmol/kg).

Table 1 below summarises the test items and dose that was administered in vivo. All test items were prepared with saline to a standard 15 ml solution.

| Material/<br>Test Item | Gadoxetate dose<br>(mmol/kg) | Gadoterate dose<br>(mmol/kg) | Gadobutrol dose[#]<br>(mmol/kg) |
|---|---|---|---|
| Gadoxetate | 0.025 | — | — |
| Gadoterate | — | 0.1 | — |
| Combo 1 | 0.025 | 0.1 | — |
| Combo 2 | 0.025 | 0.05 | — |
| Combo 3 | 0.025 | — | 0.05 |

[#]Gadobutrol formulation was diluted to 0.333 mmol/ml (equal molar concentration to gadoterate)

Dosing Regimen Rationale

The dose range of test items administered for the individual and the Combo 1 dose regimens have been selected to reflect typical clinical doses for these agents. Combo 2 and Combo 3 have a reduced cumulative gadolinium dose by lowering the dose of either gadoterate or gadobutrol (50% below the standard clinical dose=0.05 mmol/kg) whilst maintaining the dose of the gadoxetate.

In vitro relaxivity measurements were used to evaluate the efficacy (relaxivity) of the Combo formulations compared to the standalone commercial contrast agents. Longitudinal relaxation times were measured in 150 mM saline solution at 37° C. using a Minispec Mq benchtop NMR relaxometer (Bruker Instruments, Rheinstetten, Germany) operating at 60 MHz. The longitudinal relaxivity of the complexes were calculated by plotting the reciprocal of the T1 relaxation time versus the gadolinium concentration as determined via ICP-MS for each individual agent and the Combo formulations tested.

Experimental Design

The study was approved by the Universitair Ziekenhuis Brussel (UZB), Belgium local ethics committee for animal experiments on the 9 Mar. 2016 (EC number: 16-272-4). All animal experiments were carried out in accordance with the applicable laws and regulations. Naïve minipigs (Gottingen minipigs, Ellegaard Gottingen Minipigs, Denmark) were chosen as the model as its cardiac function and vascular dynamics closely resembles that of the human allowing optimal spatial and temporal resolution for the evaluation of the dynamic vascular phase.

The study consisted of five dosing groups (2 groups of contrast agent administered as single stand-alone dose; 3 groups administered with the Combo formulations). Each animal was tested once within each dosing group with a washout period of one week.

Procedures

For each MRI examination, anaesthesia was induced with a bolus of the Zoletil mixture (0.06 ml/kg, intramuscular) and maintained by an infusion of Nesdonal (0.6 ml/kg/h, intravenously (IV) administered). Test items were administered IV as a single injection via PAC unit (Port-a-cath, Power PAC II, 1.9 mm, Smiths Medical, Belgium). The test items were administered at a volume of 0.3 ml/kg using a power injector (Medrad Spectris Solaris) at a rate of 2 ml/s. Immediately following administration, 20 ml saline was passed through the tubing to flush any remaining test item.

Contrast-Enhanced MR Imaging

All MRI acquisitions were performed on a clinical 3.0 T GE MR750w scanner (GE Discovery, GE Healthcare, Waukesha, Wis.) using an abdominal phase-array surface coil positioned on the abdomen of the pigs. A multiphase dynamic 3D T1w LAVA (Liver Acquisition with Volume Acquisition) was performed using bolus timing to capture the early arterial to the late venous vascular phase using the following imaging parameters: TR/TE=2.9/1.3 ms, FA=12°, FoV=42×40 cm, matrix 220×160, slice thickness=3 mm, number of slices=40, NEX=1. The protocol also included a free-breathing navigated LAVA acquired at both pre and post administration of test item (during the delayed enhancement phase).

Image Analysis

Quantitative analysis on the time-resolved dynamic series was completed using the Advantage Windows VolumeShare 7 Workstation (GE Healthcare). Regions of interest (ROI) were placed on the aorta, the inferior vena cava (IVC), intrahepatic portal vein (PV) and normal liver parenchyma. Visual verification of all ROI locations was performed by an abdominal radiologist. For each test item, absolute signal intensity (SI) curves were analysed for each of the ROIs and expressed as peak value with inter-quartile ranges of 25% and 75%.

To calculate the vascular enhancement, relative vascular intensity (RVI) was normalised to liver parenchyma for the aorta, IVC and PV using the equation below.

$$\text{Relative Vascular Intensity (RVI)} = (SI(\text{Vessel}) - SI(\text{Liver}))/(SI(\text{Liver}))$$

Using the RVI curves, composite vascular intensity curves were derived encompassing all vascular signal from the aorta, IVC and the PV. The total vascular enhancement associated with each test item was determined by the trapezoidal rule of area under the curve (AUC), where positive signal above y=0 was included. From this, time-relative fractions at the arterial phase (AP: 30 secs), portal venous phase (PVP: 60 secs) and late venous phase (LVP: 120 secs)

were expressed as a proportion of the total vascular AUC (% RVI) and were calculated as 1-% RVI to give the percentage reduction though each phase.

For the delayed phase, a qualitative assessment was performed by an experienced radiologist for the presence or lack of enhancement pre and post-administration of test item.

In Vitro Relaxivities of Test Items

Combo 1, Combo 2 and Combo 3 were shown to have the expected relaxivities and r2/r1 ratios, based on the proportions of the various APIs (Table 2). The relaxivity measurements demonstrated all agents were viable and within standard relaxivity (r1) ranges.

Table 2 below shows the relaxivity (r1) and r2/r1 ratio measured in water at 37° C. at 60 MHz for each test item.

| Test Item | Relaxivity ($mM^{-1}s^{-1}$) in aqueous solution | Ratio r2/r1 |
|---|---|---|
| Gadoxetate | 4.7 | 1.1 |
| Gadoterate | 2.9 | 1.1 |
| Combo 1 | 3.3 | 1.2 |
| Combo 2 | 3.5 | 1.2 |
| Combo 3 | 3.7 | 1.2 |

HPLC analysis of test items.
Detector: ESA Corona, Charged Aerosol Detector and UV detector (280 nm);
Column: SeQuant ZIC-pHILIC (5 μm, 150*4.6 mm).
Sample preparation: to 30 μL test item was added $Mn(OAc)_2$ (10 μL, 10 mg/mL) then MQ-water (360 μL) followed by MeCN (600 μL)*.
Injection volume: 20 μL;
Mobile phase: 100 mM ammonium acetate (A), Acetonitrile (B).
The column was conditioned with an initial composition (of 15:85 A:B) at a flow rate of 1 mL/min for at least five minutes prior to sample injection.
Gradient:

|   | Time(min) | Flow Rate (mL/min) | % A | % B | Curve |
|---|---|---|---|---|---|
| 1. | 0 | 1.0 | 15 | 85 | 6 |
| 2. | 40 | 1.0 | 30 | 70 | 6 |
| 3. | 41 | 1.0 | 15 | 85 | 6 |
| 4. | 46 | 1.0 | 15 | 85 | 6 | where curve 6 refers to a linear gradient.
The following retention times were observed:

|   | Retention time (min) |
|---|---|
| Meglumine | 21.8 |
| GdDOTA | 23.5 |
| Gd-EOB-DTPA | 13.8 |
| Na | 17.5 |
| Gd-BT-DO3A | 24.2 |

* DOTA, EOB-DTPA and BT-DO3A were analysed indirectly as the corresponding Mn complexes.

Combo 1, Combo 2 and Combo 3 were shown to have expected API ratios in the HPLC analysis. The chemical integrity of the different APIs in the combo formulations was confirmed.

Quantitative Analysis and Signal Intensity Curves

Figure 3F:
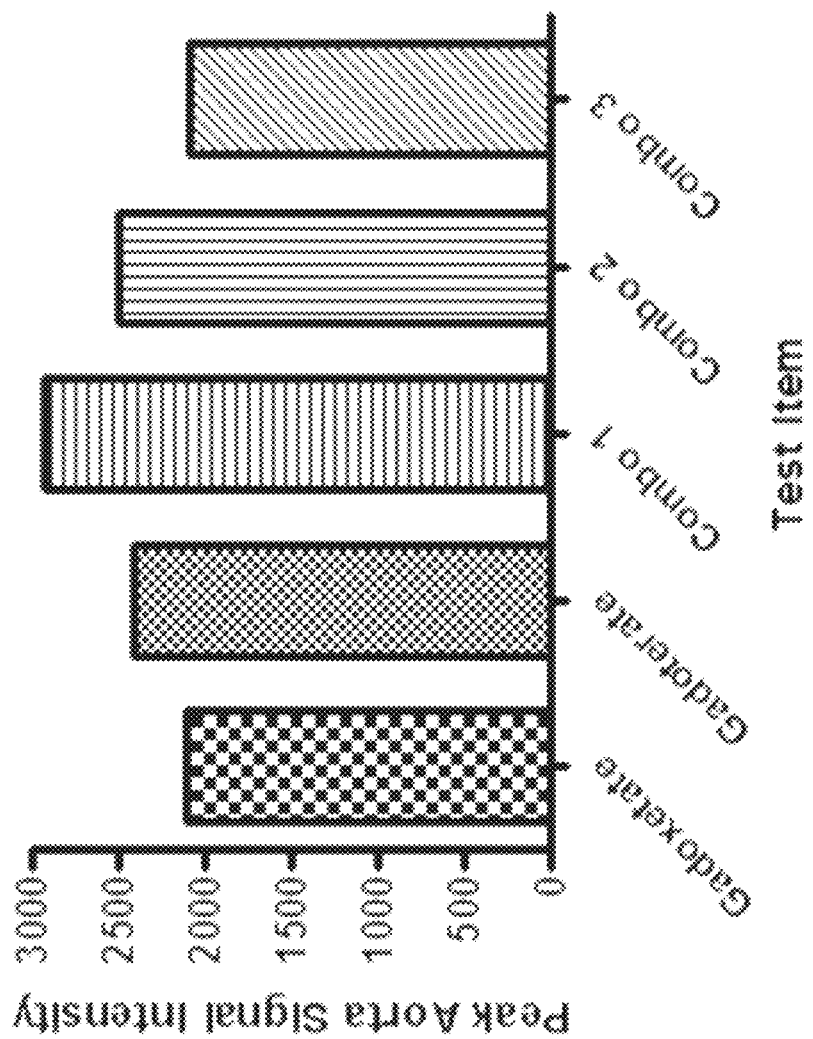
FIG. 3 illustrates the peak signal intensity curves for the aorta, inferior vena cava (IVC), portal vein (PV) and liver parenchyma (A to E) and peak arterial enhancement for each test item (F) described in the Examples below.
Figure 4F:
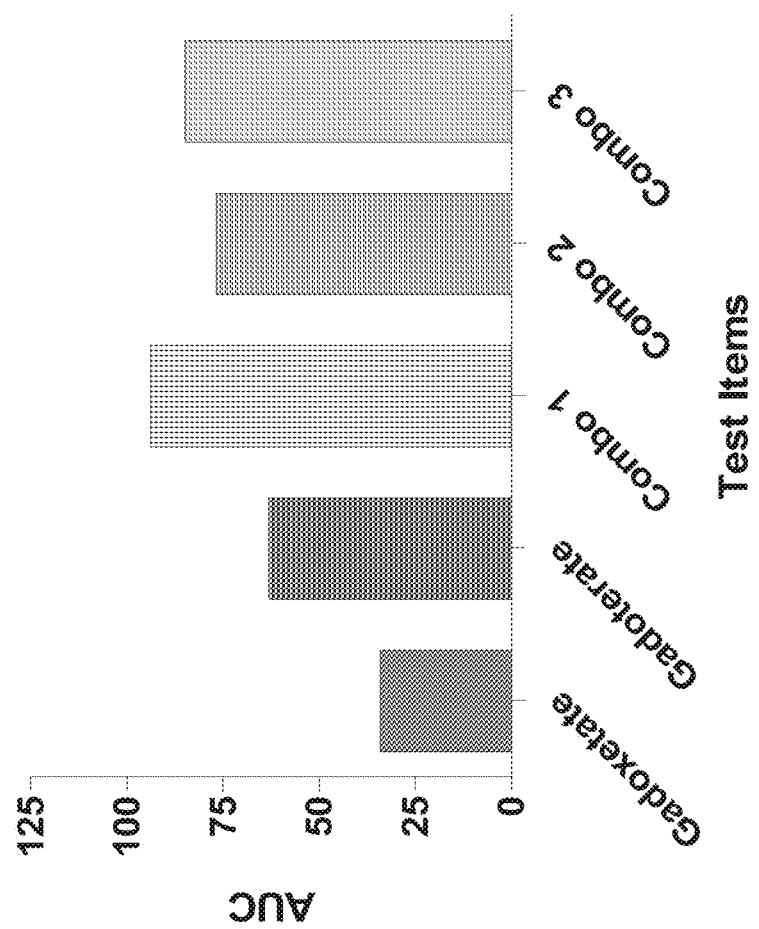
FIG. 4 illustrates the relative vascular intensity (RVI) curves for the aorta, inferior vena cava (IVC) and portal vein (PV) (A to E) and total AUC RVI for each test item (F) obtained as described in the Examples below.

For each test item, signal intensity (SI) curves were plotted for the aorta, IVC, PV and liver parenchyma ROIs as shown in FIG. 3. Peak arterial enhancement was evident with all test items, with highest SI evident from Combo 1, Combo 2 and gadoterate (Table 3) FIGS. 3A-E respectively illustrate the peak SI curves for gadoxetate, gadoterate, Combo 1, Combo 2 and Combo 3. This indicates there is comparable early arterial enhancement with all agents, including the liver specific agent gadoxetate.

Table 3 below shows the peak signal intensity from the aorta with percentile range 25% to 75% and area under the curve (AUC) from the relative vascular index (RVI) curves for each test item.

| Test Item | Gadoxetate | Gadoterate | Combo 1 | Combo 2 | Combo 3 |
|---|---|---|---|---|---|
| Peak Aorta SI (25%-75% Percentile) | 2096 (467-1064) | 2402 (225-1169) | 2926 (672-1669) | 2485 (707-1414) | 2080 (554-1304) |
| RVI AUC | 34.2 AU | 63.2 AU | 93.8 AU | 76.7 AU | 84.9 AU |

Vascular Intensity Analysis

The RVI curves were calculated for each test item and the AUC is reported in Table 3 and composite vascular intensity curves were determined to profile each test item. FIGS. 4A-E respectively illustrate the RVI curves for gadoxetate, gadoterate, Combo 1, Combo 2 and Combo 3.

Figure 5:
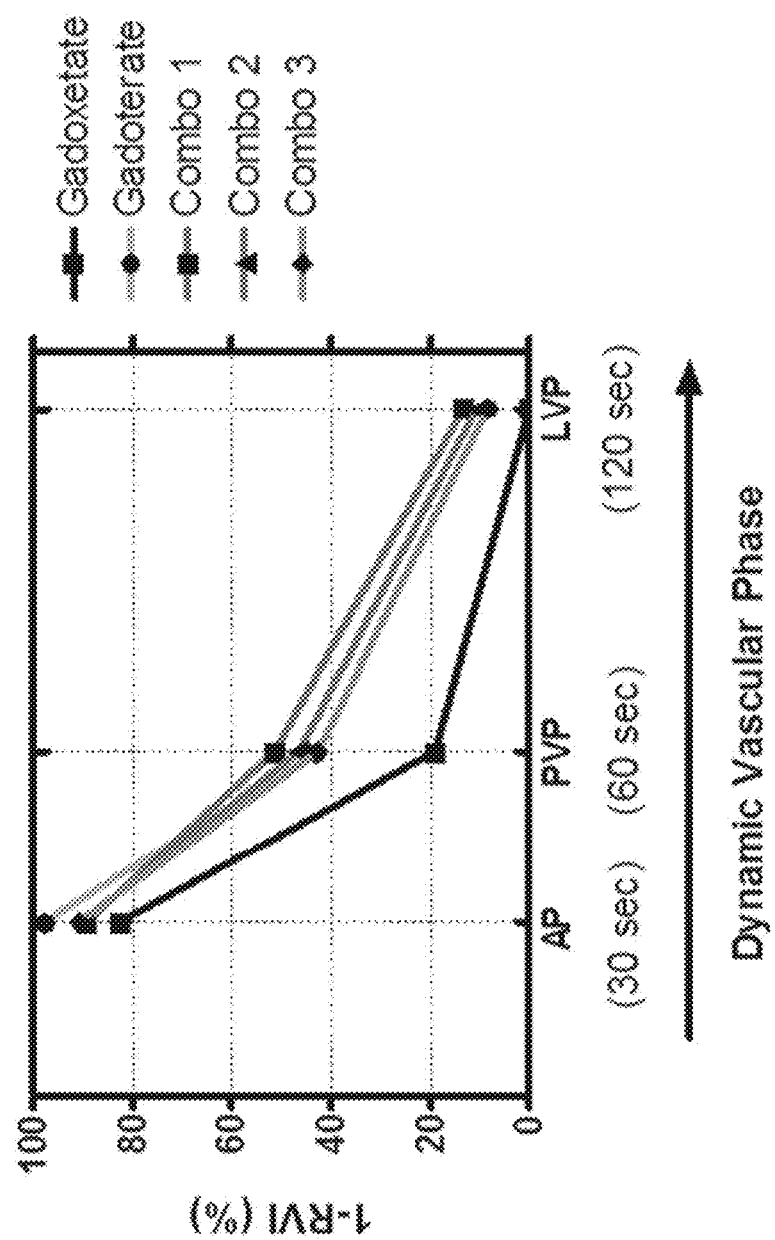
FIG. 5 shows the percentage relative vascular intensity (1-RVI %) for the arterial phase (AP) at 30 sec, the portal venous phase (PVP) at the late venous phase (LPV) 60 sec and late (PV) at 120 sec for each test item evaluated in the Examples described below.

For each of the vascular phases (AP: 30 secs, PVP: 60 secs, LVP: 120 secs), time-relative fraction was expressed as percentage relative vascular intensity (% RVI) of the total AUC for each test item (FIG. 5, Table 4).

Table 4 below shows the dynamic vascular phases expressed as percentage relative vascular intensity (1-RVI %) for the arterial phase (30 secs), the portal venous phase (60 secs) and the late venous phase (120 secs).

| Vascular Phases | Gadoxetate | Gadoterate | Combo 1 | Combo 2 | Combo 3 |
|---|---|---|---|---|---|
| AP (30 secs) | 82.4% | 97.5% | 89.2% | 90.0% | 90.7% |
| PVP (60 secs) | 19.0% | 42.8% | 51.2% | 46.6% | 42.7% |
| LVP (120 secs) | 0.0% | 8.4% | 13.3% | 10.8% | 8.4% |

Higher Relaxation Combo Agent

Two different non-specific gadolinium based contrast agents were used in this study to formulate Combo 1, Combo 2 (gadoterate) and Combo 3 (gadobutrol). Both agents showed an increase of AUC in comparison to gadoterate alone and similar % RVI for each of the vascular phases.

Qualitative Assessment for Delayed Enhancement Phase

For the delayed phases, radiological assessment indicated adequate enhancement of the liver parenchyma for Combo 1, Combo 2 and Combo 3 in comparison to gadoxetate between pre and post administration of test item.

The invention claimed is:

1. A pharmaceutical composition comprising:
   (i) a first active pharmaceutical ingredient (API) having greater than 10% hepatocellular uptake and biliary excretion, wherein the first API is gadoexetate; and,
   (ii) a second API that is a metal chelate comprising a chelant or a derivative thereof and a paramagnetic metal ion, said second API having renal excretion and a lower level of hepatocellular uptake and biliary excretion than the first API;
   (iii) a biocompatible carrier comprising excess free chelant in a form suitable for mammalian administration; wherein the ratio of said first API to said second API is from 1:10 to 4:1.

2. The pharmaceutical composition as defined in claim 1 wherein said paramagnetic metal ion is a transition metal or a lanthanide.

3. The pharmaceutical composition as defined in claim 2 wherein said paramagnetic metal ion is selected from the group comprising Eu, Gd, Dy, Ho, Cr, Mn and Fe.

4. The pharmaceutical composition as defined in claim 3 wherein said paramagnetic metal ion is selected from the group comprising Gd, Mn, Fe and Cr.

5. The pharmaceutical composition as defined in claim 4 wherein said paramagnetic metal ion is selected from the group comprising Gd(III) and Mn(II).

6. The pharmaceutical composition as defined in claim 5 wherein said paramagnetic metal ion is Gd(III).

7. The pharmaceutical composition as defined in claim 1 wherein said chelant or derivative thereof is selected from the group comprising:
   diethylenetriaminepentaacetic acid (DTPA); 4-carboxy-5, 8, 11-tris(carboxymethyl)-1-phenyl-2oxa-5, 8, 11-triazatridecan-13-oic acid (BOPTA); 1, 4, 7, 10-tetraazacyclododecan-1, 4, 7-triacetic acid (DO3A,); 1, 4, 7, 10-tetraazacyclododecan-1, 4, 7, 10-tetraactetic acid (DOTA); ethylenediaminotetraacetic acid (EDTA); 10-(2-hydroxypropyl)-1, 4, 7, 10-tetraazacyclododecan-1, 4, 7-triacetic acid (HP-DO3A); 2-methyl-1, 4, 7, 10-tetraazacyclododecan-1, 4, 7, 10-tetraacetic acid (MCTA); tetra methyl-1, 4, 7, 10-tetraazacyclododecan-1, 4, 7, 10-tetraacetic acid (DOTMA); 3, 6, 9, 15-tetraazabicyclo[9.3.1]pentadeca-1(15), 11, 13-triene-3, 6, 9-triacetic acid (PCTA,),); N, N'Bis(2-aminoethyl)-1,2-ethanediamine (TETA); 1,4,7,10-tetraazacyclotridecane-N,N',N'',N'''-tetraacetic acid (TRITA,),); 1,12-dicarbonyl, 15-(4-isothiocyanatobenzyl) 1, 4, 7, 10, 13-pentaazacyclohexadecane-N, N', N'' triaceticacid (HETA); [(2S,5S,8S,11S)-4,7-bis-carboxymethyl-2,5,8,11-tetramethyl-1,4,7,10-tetraazacyclo-dodecan-1-yl]acetic acid, (M4DO3A); 1 1-O-Phosphonomethyl-1,4,7, 1-0-tetraazacyclododecane-1, 4,7-triacetic acid (MPDO3A),); hydroxybenzyl-ethylenediamine-diacetic acid (HBED); and, N,N'-ethylenebis-[2-(o-hydroxyphenolic)glycine](EHPG); 2-[[2-[bis(carboxylatomethyl)amino]-3-(4-ethoxyphenyl)propyl]-[2-[bis(carboxylatomethyl)amino]ethyl]amino]acetate (EOB-DTPA); 10-[(1SR,2RS)-2,3-dihydroxy-1-hydroxymethylpropyl]-1,4,7,10-tetraazacyclododecane-1,4,7-triacetic acid (BT-DO3A); 2-[bis[2-[carboxylatomethyl-[2-(methylamino)-2-oxoethyl]amino]ethyl]amino]acetate (DTPA-BMA); and, 2-[bis[2-[carboxylatomethyl-[2-(2-methoxyethylamino)-2-oxoethyl]amino]ethyl]amino]acetate (DTPA-BMEA); N-[2-[bis(carboxymethyl)amino]-3-(4-ethoxyphenyl)propyl]-N-[2-[bis(carboxymethyl)-amino]ethyl]-L-glycine (EOB-DTPA), N,N-bis[2-[bis(carboxymethyl)amino]-ethyl]-L-glutamic acid (DTPA-Glu), N,N-bis[2-[bis(carboxymethyl)amino]-ethyl]-L-lysine (DTPA-Lys), N,N-bis[2-[carboxymethyl[(methylcarbamoyl)methyl]amino]-ethyl] glycine (DTPA-BMA); 1,4,7,10-tetraazacyclododecane-N,N',N'',N'''-tetraacetic acid mono-(N-hydroxysuccinimidyl) ester (DOTA-NHS); [(2S,5S, 8S, 11S)-4,7,10-tris-carboxymethyl-2,5,8,11-tetramethyl-1,4,7,10-tetraazacyclododecan-1-yl]acetic acid (M4DOTA); (R)-2-[(2S,5S,8S,11S)-4,7,10-tris-((R)-1-carboxyethyl)-2,5,8,11-tetramethyl-1,4,7,10-tetraazacyclododecan-1-yl]propionic acid (M4DOTMA); PCTA12; cyclo-PCTA12; N, N'-Bis(2-aminoethyl)-1,2-ethanediamine-N-hydroxy-succinimide ester (TETA-NHS).

8. A dose of a pharmaceutical composition to be administered to a subject wherein said pharmaceutical composition is as defined in claim 1 and wherein said dose comprises between 0.01-0.04 mmol per kilogram of said subject of said first API and between 0.01-0.1 mmol per kilogram of said subject of said second API with the proviso that the combined dose of said first API and second API does not exceed 0.125 mmol per kilogram of said subject.

9. The dose as defined in claim 8 wherein the combined dose of said first API and second API is less than 0.125 mmol per kilogram of said subject.

10. The dose as defined in claim 8 which comprises between 0.02-0.03 mmol per kilogram of said subject of said first API.

11. The dose as defined in claim 8 which comprises between 0.025-0.1 mmol per kilogram of said subject of said second API wherein said second API has a relaxivity ≥3 mM−1 s−1 at field strengths of 1.5-3 T.

12. The dose as defined in claim 8 which comprises between 0.02-0.09 mmol per kilogram of said subject of said second API wherein said second API has a relaxivity ≥5 mM−1 s−1 at field strengths of 1.5-3 T.

13. The dose as defined in claim 8 which comprises between 0.02-0.07 mmol per kilogram of said subject of said second API wherein said second API has a relaxivity ≥7 mM−1 s−1 and field strengths of 1.5-3 T.

14. The dose as defined in claim 8 which comprises between 0.01-0.06 mmol per kilogram of said subject of said second API wherein said second API has a relaxivity ≥9 mM−1 s−1 at field strengths of 1.5-3 T.

15. The dose as defined in claim 8 which comprises 0.025 mmol per kilogram of said subject of said first API.

16. The dose as defined in claim 8 which comprises 0.1 mmol per kilogram of said subject of said second API.

17. The dose as defined in claim 8 which comprises 0.05 mmol per kilogram of said subject of said second API.

18. The dose as defined in claim 8 wherein said subject is a living human or non-human animal body.

19. A method comprising:
   (a) administering a dose of a pharmaceutical composition to a subject wherein said dose comprises:
   (i) a first active pharmaceutical ingredient (API) having hepatocellular uptake and biliary excretion, wherein the first API is gadoexetate; and,
   (ii) a second API that is a metal chelate comprising a chelant or a derivative thereof and a paramagnetic metal ion, said second API having renal excretion and a lower level of hepatocellular uptake and biliary excretion than the first API;
   (iii) a biocompatible carrier comprising excess free chelant in a form suitable for mammalian administration;

wherein the ratio of said first API to said second API is from 1:10 to 4:1, (b) carrying out magnetic resonance imaging (MRI) on said subject following said administering step wherein magnetic resonance (MR) signals are detected from the subject or parts of the subject into which the dose has distributed; and (c) generating MR images and/or MR spectra from the detected MR signals.

20. The method as defined in claim 19, wherein said subject is a living human or nonhuman animal body.

21. The method as defined in claim 19, wherein said composition is administered in an amount suitable to enhance the contrast in the method of MR imaging.

22. The pharmaceutical composition of claim 1, wherein the proportion of hepatobiliary clearance of said first API is between 10-50%.

23. The pharmaceutical composition of claim 1, wherein the proportion of hepatobiliary clearance of said first API is between 20-50%.

24. The pharmaceutical composition of claim 1, wherein the proportion of hepatobiliary clearance of said first API is between 30-50%.

25. The pharmaceutical composition of claim 1, wherein the proportion of hepatobiliary clearance of said first API is between 40-50%.

26. The pharmaceutical composition of claim 22, wherein the proportion of hepatobiliary clearance of said second API is no more than 5%.

27. The pharmaceutical composition of claim 22, wherein the proportion of hepatobiliary clearance of said second API is no more than 5%.

28. The pharmaceutical composition of claim 27, wherein second API is selected from Gadoterate or Gadobutrol.

* * * * *